US010940129B2

(12) United States Patent
Ott

(10) Patent No.: US 10,940,129 B2
(45) Date of Patent: Mar. 9, 2021

(54) METHOD OF TREATMENT FOR REDUCING PAIN SENSITIZATION

(71) Applicant: David Michael Ott, Berkeley, CA (US)

(72) Inventor: David Michael Ott, Berkeley, CA (US)

( * ) Notice: Subject to any disclaimer, the term of this patent is extended or adjusted under 35 U.S.C. 154(b) by 233 days.

(21) Appl. No.: 16/107,621

(22) Filed: Aug. 21, 2018

(65) Prior Publication Data

US 2020/0061008 A1 Feb. 27, 2020

(51) Int. Cl.
| *A61K 31/198* | (2006.01) |
| *A61P 25/02* | (2006.01) |
| *A61P 25/00* | (2006.01) |
| *A61K 9/00* | (2006.01) |
| *A23L 33/10* | (2016.01) |
| *A23L 2/52* | (2006.01) |
| *A61K 36/88* | (2006.01) |

(52) U.S. Cl.
CPC .............. *A61K 31/198* (2013.01); *A23L 2/52* (2013.01); *A23L 33/10* (2016.08); *A61K 9/0053* (2013.01); *A61K 9/0095* (2013.01); *A61K 36/88* (2013.01); *A61P 25/00* (2018.01); *A61P 25/02* (2018.01); *A23V 2002/00* (2013.01)

(58) Field of Classification Search
CPC ............................. A61K 31/198; A61P 25/02
USPC ......................................................... 514/562
See application file for complete search history.

(56) References Cited

U.S. PATENT DOCUMENTS

| 7,678,833 | B2* | 3/2010 | Ott | ....................... A61K 31/095 |
| | | | | 424/439 |
| 8,217,084 | B2* | 7/2012 | Ott | ....................... A61K 31/255 |
| | | | | 424/439 |
| 8,222,299 | B2* | 7/2012 | Ott | ....................... A61K 31/255 |
| | | | | 514/706 |

OTHER PUBLICATIONS

Crabb et al, J. Clin. Invest 1989, vol. 83, pp. 314-316. (Year: 1989).*
Delta Nutrassentials webpage printout of https://www.prnewswire.com/news-releases/delta-nutrassentials-launches-essential-ad2-to-reduce-acetaldehyde-accumulation-in-1-billion-people-globally-who-suffer-from-aldh2-deficiency-and-asian-flush-300368873.html (Year: 2016).*
Galer and Grace, Annals of Translational Medicine 2015, vol. 3 (S1): S23, pp. 1-3. (Year: 2015).*
Droge, Pharmacology 1993, vol. 46, pp. 61-63. (Year: 1993).*
Octaviana, excerpt from Demystifying Polyneuropathy—Recent Advances and New Directions 2018, pp. 1-11. (Year: 2018).*

* cited by examiner

*Primary Examiner* — Craig D Ricci
*Assistant Examiner* — Janet L. Coppins

(57) ABSTRACT

The present disclosure relates to the use of lipophilic mercaptans for the treatment of pain sensitization. The lipophilic mercaptans disclosed can be used to decrease the formation of protein-aldehyde adducts within nociceptive nerves, thereby reducing sensitization to pain.

15 Claims, 11 Drawing Sheets
(1 of 11 Drawing Sheet(s) Filed in Color)

Acetylaldehyde

Acrolein

Allicin

Allyl Isothiocyannate (AITC)

Cinnamaldehyde

Diallyl disulfide

Formaldehyde

Ligustilide 4-hydroxy-2-nonenal (HNE)

Perilla ketone

Piperine

Umbellulone

Velleral

15d-PGJ$_2$

Putative cytoplasmic cysteines

4-HNE + Cysteine protein adduct formation

Protein repair and 4-HNE + Allyl mercaptan conjugate formation

4-HNE + Lysine protein adduct formation

Protein repair and 4-HNE + Allyl mercaptan conjugate formation

Unsaturated fatty acid (10:1ω6)

Peroxidized Fatty Acid

Aldehyde (Hexanal)

Aldehyde (Succinic semialdehyde)

Allyl Mercaptan

Propyl Mercaptan

Hydralazine

Phenlzine

Gabapentin (in lipid)

Gabapentin (in water)

S-(3-((2-acetamido-2-carboxyethyl)-disulfanyl)propyl)-N-acetylcysteine

S-(1-((2-acetamido-2-carboxyethyl)-disulfanyl)propan-2-yl)-N-acetylcysteine

S-(1-((2-acetamido-2-carboxyethyl)-disulfanyl)propan-2-yl)-N-acetylcysteine anion

METHOD OF TREATMENT FOR REDUCING PAIN SENSITIZATION

FIELD OF THE INVENTION

The invention relates to the use of organosulfur compounds for the treatment of pain sensitization. More specifically, a class of lipophilic mercaptans is disclosed which can be used to decrease the formation of protein-aldehyde adducts within nociceptive nerves, thereby reducing sensitization to pain. Examples of use include dietary supplements and drugs that are suitable for oral administration to humans who suffer from pain sensitization.

BACKGROUND OF THE INVENTION

1. Definitions, Glossary, and Abbreviations

Note: Unless otherwise stated, all amino acids mentioned within the specification or the claims are of the L-isomer.

Acrolein: The smallest and most reactive alpha,beta-unsaturated aldehyde. As an environmental toxin, acrolein is commonly present in smoke from fires, including cigarette smoke. Endogenous acrolein is a spontaneous breakdown product of peroxidized fatty acids in the body. FIG. 3A.

Acute Pain: Pain at the time of stimulus or injury and shortly thereafter.

Administer: The willful treatment with a therapeutic agent.

Allyl Isothiocyanate; AITC: The compound that gives mustards their pungent taste. AITC can elicit acute pain when applied to skin. FIG. 3C.

Aldehyde Dehydrogenase 2; ALDH2: The mitochondrial enzyme that detoxifies aldehydes by converting them to less toxic acids. The gene for the protein ALDH2 is ALDH2. A common mutation of ALDH2 is ALDH2-2 (also known as ALDH2*2 or ALDH2$^2$). In human ALDH2-2, this mutation is a Glu to Lys substitution located 487 residues from the amino terminus of the mature subunit.

Allicin; (diallyl thiosulfinate): The principal thiosulfinate that is formed when garlic is crushed. Allicin is responsible for the burning sensation when raw garlic is bitten into. FIG. 3B.

Allodynia: The condition in which an ordinarily painless stimulus, when perceived, is experienced as being painful. Allodynia is a symptom of pain sensitization.

Allyl mercaptan: The mercaptan that is produced when allicin is metabolized. In the present exposition, allyl mercaptan is the model lipophilic mercaptan (preferring a lipid environment to an aqueous environment). FIG. 12A.

In general, a compound is referred to herein as a "model" compound when it is representative of a more general class of compounds defined herein.

Biothiol: Any thiol that is commonly found in biological systems. The most common biothiols are cysteine and glutathione.

Chronic Pain: Pain that persists long after the initial cause of pain has been removed, e.g. pain that extends beyond the expected period of healing.

Dorsal Root Ganglion; DRG: A cluster of the cell bodies of sensory neurons, located adjacent to a pair of spinal vertebrae.

Drug: In the present context, a "drug" is a composition intended for oral administration that requires FDA approval as a drug. This is in contrast to a "dietary supplement", which only needs to meet the FDA requirements for dietary supplements.

Formalin: A dilution of formaldehyde in water, used for pain stimulus in animal testing for various models of pain. FIG. 3F.

Glutathione: a tripeptide composed of the amino acids glutamate, cysteine, and glycine. Glutathione is an important antioxidant. Glutathione is also important for the detoxification of various compounds, especially in conjunction with glutathione transferase enzymes.

4-hydroxy-2-nonenal; 4-HNE: An alpha,beta-unsaturated aldehyde that has been extensively researched. Endogenous 4-HNE is a spontaneous breakdown product of peroxidized fatty acids in the body. FIG. 3H. In the present exposition, 4-HNE is the model alpha,beta-unsaturated aldehyde.

Hyperalgesia: An excessive sensitivity to pain. Also known as pain hypersensitivity. Hyperalagesia is a symptom of pain sensitization.

Lipophilic molecule: Attracted to lipids. A molecule is lipophilic if it preferentially partitions into the oily side of an oil and water system. For example, allyl mercaptan has a partition coefficient (Log P) of 1.2, which indicates that its concentration on the oily side is approximately 16 times its concentration on the aqueous side of an oil and water system.

Mercaptan: A small molecule with the general formula RSH where R is an organic radical. Mercaptans are the subset of thiols which are small molecules and only have one terminal sulfhydryl (SH) group. Mercaptans are typically volatile and very smelly.

Molecular Mass in Daltons: The mass of a molecule expressed in units of $\frac{1}{12}$ of the weight of one atom of the isotope carbon-12.

Nociception: The stimulus-response process involving the stimulation of pain-sensing nerves, the transmission of impulses along these nerves to the central nervous system (e.g. the spinal cord) and then to the brain, where the stimulus is perceived as pain.

NSAID: Nonsteroidal anti-inflammatory drugs; NSAID: A class of drugs that reduce pain, decrease fever, prevent blood clots and decrease inflammation.

Organosulfur compound: A molecule that contains carbon-carbon bonds, carbon-hydrogen bonds, at least one covalently bound sulfur atom, and optionally other covalently bound atoms such as nitrogen or oxygen atoms.

Pain sensitization: A condition in which sensitivity to pain is increased. Allodynia and hyperalgesia are symptoms of pain sensitization.

Partition coefficient; Log P: The ratio of the concentrations of a solute between two solvents. When one of the solvents is non-polar and the other is water, this is a measure of lipophilicity and the logarithm of the ratio is Log P. Unless otherwise specified, the Log P values reported herein are from the National Library of Medicine "PubChem" database (which uses the XLogP3-AA algorithm for Log P determination).

Propyl mercaptan; chemical name 1-PropaneThiol: Propyl mercaptan is a metabolite that is produced when onions are consumed. FIG. 12B.

Protein-aldehyde adduct: a protein that has been modified by the addition of an aldehyde. For whatever reason, this type of conjugate is commonly called an "adduct" when a protein is involved.

Protein carbonylation: The net addition of a carbonyl group onto a protein, including protein carbonyls that are formed by the addition of an aldehyde.

Radical; R: A group of atoms which behaves as a unit and has one unpaired electron. A radical is normally connected by a single bond to the rest of a molecule.

Secondary hyperalgesia: An increase in sensitivity to pain at locations within a moderate distance away from the site where the painful stimulus was applied. For example, where a painful injection of formalin in the foot of a rat produces pain hypersensitivity on the same foot 2 cm away.

Thiol: Any molecule that includes one or more terminal sulfhydryl (SH). Mercaptans (RSH) are the subset of thiols which are small molecules and only have one terminal sulfhydryl (SH).

Transglycation: The transfer of an aldehyde (such as glucose) from one molecule to another. For example, the transfer of a protein-aldehyde adduct (i.e. the aldehyde) from a protein molecule to a mercaptan molecule, repairing the protein and forming a mercaptan-aldehyde conjugate molecule.

Transient Receptor Protein A1; TRPA1: A non-selective cation channel expressed by some sensory neurons of the pain pathway. TRPA1 is sensitive to certain pungent compounds (e.g. AITC from mustard), cold temperatures and mechanical stress. Almost all neurons that express TRPA1 also express TRPV1. For convenience, TRPA1 is sometimes referred to as a "calcium channel" due to the importance of calcium to its function.

Transient Receptor Protein V1; TRPV1: A nonselective cation channel expressed by some sensory neurons of the pain pathway. Sensitive to certain pungent compounds (e.g. capsaicin from hot peppers) and hot temperatures. Approximately 30% of neurons that express TRPV1 also express TRPA1.

Treatment for pain sensitization: The administration of a therapeutic composition to a subject for the purpose of reducing pain sensitivity towards the subject's basil sensitivity to pain. Those in need of treatment may include those already with the disease, condition or disorder as well as those prone to have the disease, condition or disorder.

von Frey hairs: A von Frey hair provides a means to apply a calibrated mechanical force at a point on the skin in order to determine sensory threshold sensitivity or to test for pain perception. Each hair is a nylon filament with a rounded tip and a precise "bending" force such that when it is used to poke the skin with enough force to cause the hair to at least slightly bend, the force to the skin remains constant. A set of handles with differing diameter filaments allow a calibrated set of pressures to be used for the test.

2. References

Andersson, D. et al. Transient receptor potential A1 is a sensory receptor for multiple products of oxidative stress. The Journal of Neuroscience 28:2485 (2008).

Bai, L. et al. Attenuation of mouse somatic and emotional inflammatory pain by Hydralazine through scavenging acrolein and inhibiting neuronal activation. Pain Physician 15; 311 (2012).

Bahlis, N. et al. Feasibility and correlates of arsenic trioxide combined with ascorbic acid-mediated depletion of intracellular glutathione for the treatment of relapsed/refractory multiple myeloma. Clinical Cancer Research 8:3658 (2002).

Bang, S. et al. Transient receptor potential A1 mediates acetylaldehyde-evoked pain sensation. European Journal of Neuroscience 26:2516 (2007).

Banke, T. et al. Dynamic changes in the TRPA1 selectivity filter lead to progressive but reversible pore dilation. American Journal of Physiology Cell Physiology 298: C1457 (2010).

Baraldi, P. et al. Transient Receptor Potential Ankyrin 1 (TRPA1) channel as emerging target for novel analgesics and anti-inflammatory agents. Journal of Medicinal Chemistry 53:5085 (2010).

Bautista, D. et al. TRPA1: A gatekeeper for inflammation. Annual Reviews of Physiology 75:181 (2013).

Bahlis, N. et al. Feasibility and correlates of arsenic trioxide combined with ascorbic acid-mediated depletion of intracellular glutathione for the treatment of relapsed/refractory multiple myeloma. Clinical Cancer Research 8:3658 (2002).

Brookes, P. et al. Calcium, ATP, and ROS: a mitochondrial love-hate triangle. American Journal of Physiology Cell Physiology 287:C817 (2004).

Chen, C. et al. Activation of aldehyde dehydrogenase-2 reduces ischemic damage to the heart. Science 321:1493 (2008).

Chen, C. et al. Targeting aldehyde dehydrogenase 2: New therapeutic opportunities. Physiological Reviews 94:1 (2014).

Chen, J. et al. Pore dilation occurs in TRPA1 but not in TRPM8 channels. Molecular Pain 5:3 (2009).

del Camino, D. et al. TRPA1 contributes to cold hypersensitivity. The Journal of Neuroscience 30:15174 (2010).

Galer, E. et al. Reactive aldehydes: a new player in inflammatory pain. Annals of Translational Medicine 3(S1):S23 (2015).

Gaudet, R. A primer on ankyrin repeat function in TRP channels and beyond. Molecular BioSystems 4:372 (2008).

Goa, K. et al. Gabapentin—A review of its pharmacological properties and clinical potential in epilepsy. Drugs 46:409 (1993).

Goedde, H. et al. Aldehyde dehydrogenase polymorphism in North American, South American, and Mexican Indian populations. American Journal of Human Genetics 38:395 (1986).

Grace, P. et al. Morphine paradoxically prolongs neuropathic pain in rats by amplifying spinal NLRP3 inflammasome activation. Proceedings of the National Academy of Sciences 113:E3441 (2016).

Hinman, A. et al. TRP channel activation by reversible covalent modification. Proceedings of the National Academy of Sciences 103:19564 (2006).

Keeble, J. et al. Hydrogen peroxide is a novel mediator of inflammatory hyperalgesia, acting via transient receptor potential vanilloid 1-dependent and independent mechanisms. Pain 141:135 (2009).

Koivisto, A. et al. TRPA1: A transducer and amplifier of pain and inflammation. Basic & Clinical Pharmacology & Toxicology 114:50 (2014).

Krebs, E. et al. Effect of Opioid vs Nonopioid Medications on Pain-Related Function in Patients With Chronic Back Pain or Hip or Knee Osteoarthritis Pain: The SPACE Randomized Clinical Trial. Journal of the American Medical Association 319:872 (2018).

Li, L. et al. Heparanase overexpression reduces carrageenan-induced mechanical and cold hypersensitivity in mice. Neuroscience Letters 511:4 (2012).

Machado, G. et al. Efficacy and safety of paracetamol for spinal pain and osteoarthritis: systematic review and meta-analysis of randomized placebo controlled trials. British Medical Journal 350:H1225 (2015).

Machado, G. et al. Non-steroidal anti-inflammatory drugs for spinal pain: a systematic review and meta-analysis. Annals of the rheumatic diseases 76:1269 (2017).

McMahon, S. et al. Immune and glial cell factors as pain mediators and modulators. Experimental Neurology 192: 444 (2005).

McNamara, C. et al. TRPA1 mediates formalin-induced pain. Proceedings of the National Academy of Science 104:13525 (2007).

Moharic, M. et al. Tactile thresholds in healthy subjects. Zdravniski vestnik 83:581 (2014).

Nakagawa, S. et al. Prevention of liver damage by aged garlic extract and its components in mice. Phytotherapy Research 3:50 (1989).

Novoradovsky, A. et al. Mitochondrial aldehyde dehydrogenase polymorphism in Asian and American Indian populations: Detection of new ALDH2 alleles. Alcoholic Clinical and Environmental Research 19:1105 (1995).

Obata, K. et al. TRPA1 induced in sensory neurons contributes to cold hyperalgesia after inflammation and nerve injury. The Journal of Clinical Investigation 115:2393 (2005).

O'Mullan, G. et al. Sniffing Out the Truth; The New York Times, Jan. 21, 2007.

Paulsen, C. et al. Structure of the TRPA1 ion channel suggests regulatory mechanisms. Nature 520:511 (2015).

Perez-Miller, S. et al. Alda-1 is an agonist and chemical chaperone for the common human aldehyde dehydrogenase 2 variant. Nature Structural & Molecular Biology 17:159 (2010).

Pizzo, M. et al. Alleviating Suffering 101—Pain Relief in the United States. The New England Journal of Medicine 366:197 (2012).

Puri, R. et al. Inactivation of fructose-1,6-bisphosphate by o-phthalaldehyde. Biochemical and Biophysical Research Communications 150:1088 (1988).

Riquelme, I et el. Abnormal pressure pain, touch sensitivity, proprioception, and manual dexterity in children with Autism Spectrum Disorders. Neural Plasticity—Article ID 1723401 (2016).

Salat, K. et al. Transient Receptor Potential channels—Emerging novel drug targets for the treatment of pain. Current Medicinal Chemistry 20:1409 (2013).

Sawada, Y. et al. Activation of transient receptor potential ankyrin 1 by hydrogen peroxide. European Journal of Neuroscience 27:1131 (2008).

Schauenstein, E. et al. Aldehydes in Biological Systems—Their Natural Occurrence and Biological Activities. Pion Limited, London (1977).

Song, M. et al. The antidepressant phenelzine protect neurons and astrocytes against formaldehyde-induced toxicity. Journal of Neurochemistry 14:1405 (2010).

Szwergold, B. et al. Transglycation—A potential new mechanism for deglycation of Schiff's bases. Annals of the New York Academy of Sciences 1043:845 (2005).

Trevisani, M. et al. 4-Hydroxynonenal, an endogenous aldehyde, causes pain and neurogenic inflammation through activation of the irritant receptor TRPA1. Proceedings of the National Academy of Sciences 104:13519 (2007).

U.S. Pat. No. 7,678,833; D. M. Ott; Method to Increase the Bioavailability of Cysteine. U.S. Pat. No. 7,678,833 (2010).

U.S. Pat. No. 8,222,299; D. M. Ott; Organosulfur prodrugs for the prevention and treatment of infectious diseases. U.S. Pat. No. 8,222,299 (2012).

U.S. Pat. No. 9,456,999; D. M. Ott; Organosulfur compounds for the prevention and treatment of neurodegenerative diseases. U.S. Pat. No. 9,456,999 (2016).

U.S. Pat. No. 9,545,393; Zambelli et al. Methods and compositions for treating pain. U.S. Pat. No. 9,545,393 (2017).

Wang, L. et al. Identification of in vivo disulfide conformation of TRPA1 ion channel. Journal of Biological Chemistry 287:6169 (2012).

Wang, Y. et al. The nociceptor ion channel TRPA1 is potentiated and inactivated by permeating calcium ions. Journal of Biological Chemistry 283:32691 (2008).

Wei, H. et al. Roles of cutaneous versus spinal TRPA1 channels in mechanical hypersensitivity in the diabetic or mustard oil-treated non-diabetic rat. Neuropharmacology 58:578 (2010).

Zambelli, V. et al. Aldehyde dehydrogenase-2 regulates nociception in rodent models of acute inflammatory pain. Science Translational Medicine 251:251RA118 (2014).

3. Description of the Published Art 3.1 There is Currently No Adequate Treatment for Chronic Pain.

There is an enormous need for improved treatments for chronic pain. The magnitude of pain in the USA is astounding. More than 116 million Americans have pain that persists for weeks to years. USA expenditures on pain are higher than those for cancer, heart disease, and diabetes combined, at approximately $560 billion annually. Impediments to relief include the prevalence of outmoded or unscientific knowledge and attitudes about pain [Pizzo, 2012].

A recent randomized clinical trial compared the effect of opioid vs non-opioid medications on pain-related function in patients with chronic back pain or hip or knee osteoarthritis pain. The 120 patients in the opioid group started taking immediate-release opioids (e.g. morphine IR) but the addition a sustained-action opioid (e.g. oxycodone SA) was also an option based on patient needs and preferences. The 120 patients in the non-opioid group started on acetaminophen and NSAIDs, but the addition of adjuvant oral medications (e.g. gabapentin) or topical analgesics (e.g. capsaicin) was also an option based on patient needs and preferences. At 12 months, the non-opioid group had significantly lower pain intensity (3.5 on a scale of 0-10) compared to the opioid group (4.0). The non-opioid group also had significantly fewer medication-related symptoms than the opioid group (e.g. half the rate of "Primary Adverse Outcomes"). But there was no significant difference in pain related function between the two groups over 12 months. Their conclusion is "results do not support initiation of opioid therapy for moderate to severe chronic back pain or hip or knee osteoarthritis pain" [Krebs, 2018].

A recent study monitored the long term effect of a 5 day course of morphine treatment that started 10 days after chronic constriction injury to the spinal cord of male rats. The morphine treatment had the remarkable effect of more than doubling the duration of injury-related allodynia (pain from ordinarily painless stimulus), which persisted for months after the morphine treatment ceased (FIG. 1A of Grace). This was determined to be due to morphine having activated innate immunity. The persistent sensitization was dependent on IL-1β signaling and the activation of microglia in the spinal cord [Grace, 2016].

But even though acetaminophen and NSAIDs are preferable to opioids for treating chronic pain, a meta-analysis concluded that the difference in outcomes between acetaminophen treatment and placebo groups is not clinically important [Machado, 2015].

A similar meta-analysis concluded that the difference in outcomes between NSAID treatment and placebo groups is not clinically important [Machado, 2017].

Clearly, a better way to treat chronic pain is needed.

An illustration of "Pain pathways as drug targets for commonly used analgesic drugs" is shown in FIG. 2 (from FIG. 2 of [Salat, 2013]).

3.2 New Knowledge About the Causes of Pain

Modern methods greatly increase the amount of physiological detail which can be measured or observed, in some cases causing major revisions to long-held beliefs. This is especially true now that genetic information is available for the entire human genome.

Diseases associated with gross genetic defects have been known for decades, but only a small minority of the population will inherit a specific genetic defect which, in and of itself, produces a disease. Most genetic diseases are now known to be associated with a combination of genetic alleles (none of which can individually cause the disease), or the combination of one or more genetic alleles with environmental factors.

3.2.1 The Role of the ALDH2 Protein in Pain Sensitivity.

An exception to this is the ALDH2 gene. Mutations in this single gene have long been known to impair the metabolism of alcohol, increasing its toxicity to the affected populations. Normally, ethanol is converted to acetaldehyde by the enzyme "Alcohol Dehydrogenase", and then the enzyme "Aldehyde Dehydrogenase 2" (ALDH2) converts the acetaldehyde to acetate. But if ALDH2 is not functional, the toxic acetaldehyde accumulates.

Genetic polymorphisms of human ALDH2 have been well surveyed among a wide range of ethnic groups. The most relevant ALDH2 variant is the ALDH2*2 allele, which is found in ~40% of East Asians (i.e. Chinese, Japanese, Koreans, and Taiwanese), totaling ~560 million people (~8% of the world's population, making it the most common human enzyme deficiency). ALDH2*2 codes for a dominant-negative variant that reduces net ALDH2 enzymatic activity by 60 to 80% in heterozygotes (ALDH2*1/*2) and by ~95% in homozygotes (ALDH2*2/*2) when compared to normal ALDH2 (ALDH2*1/*1) [Zambelli, 2014].

One set of effects of the impaired ALDH2 activity for this population is the characteristic facial flushing, headaches, nausea, dizziness, and cardiac palpitations after consumption of alcoholic beverages. Another effect is pain hypersensitivity [Chen, 2014]. Mutations to ALDH2 also occur in other populations (e.g. American Indians and especially South American Indians) [Goedde, 1986], [Novoradovsky, 1995].

I have some personal experience with this, having been acquainted with a Chinese woman (a friend of my father's) who has pain hypersensitivity. She is also hypersensitive to cold, frequently wearing a sweater (even in sunny Southern California) and using chemical hand-warmers.

In addition to its critical role in alcohol metabolism, ALDH2 is capable of metabolizing various other aldehydes, thus providing an important protective enzymatic function against these toxic agents. In particular, ALDH2 plays a key role in oxidizing endogenous aldehydic products that arise from lipid peroxidation such as acrolein and 4-hydroxy-2-nonenal (4-HNE), as well as environmental aldehydes such as acrolein (present in tobacco smoke and in car exhaust) [Chen, 2014].

The ALDH2*2 protein has been proposed as an attractive drug target for the prevention and treatment of inflammatory pain [Galer, 2015]. Furthermore, a variety of diseases are associated with the inability of ALDH2*2 to sufficiently eliminate toxic aldehydes, including cardiac ischemia and reperfusion injury, non-insulin-dependent diabetes mellitus (NIDDM), diabetic pathology, Alzheimer's, upper aerodigestive track (UADT) cancer, and osteoporosis [Chen, 2014], [Perez-Miller, 2010].

3.2.2 Pharmacological Restoration of ALDH2*2 Activity.

An experimental drug ("Alda-1") has been developed that activates the aldehyde dehydrogenase activity of both wild-type ALDH2*1 and mutant ALDH2*2 enzymes [U.S. Pat. No. 9,545,393]. Alda-1 binds either form of ALDH2 near the exit of the substrate binding tunnel, at a position that overlaps an inhibitory site, which doubles the efficiency of ALDH2*1 and also provides structural stability to the ALDH2*2 enzyme [Perez-Miller, 2010]. Alda-1 increases the activity of ALDH2*2 by 2.2-fold [Chen, 2008].

3.2.3 Animal Testing of Alda-1 Yields Interesting Results.

This drug was validated in a mouse model which incorporated one copy of the same mutation that is present in human ALDH2*2. The ALDH2*1/*2 heterozygous mutant mice (when untreated) exhibited the expected defect in detoxifying aldehydes (e.g. acetaldehyde, which was 5× higher after alcohol consumption compared to ALDH2*1/*1 wild type mice, the same ratio as observed in humans with heterozygous mutation). Liver tests also confirmed that ALDH2 activity in the mutant mice was only 20% of that of wild-type animals [Zambelli, 2014, which is hereby included by reference].

When tested for pain, a single injection into a rear paw of 100 ng of acetaldehyde produced 5 seconds of licking or flinching in the mutant mice compared to 4 seconds for the wild-type mice (FIG. 5D of Zambelli, 2014), a difference that was considered biologically insignificant by the authors. But when tested for mechanical pain sensitivity ("nociceptive threshold" for pressure to the paw), the mutant mice were 4 times more sensitive to pressure (FIG. 5E of Zambelli, 2014). In other words, the chemical treatment (injection of an aldehyde) produced at most a small pain response in itself, but the big effect was that it made the mutant mice significantly more sensitive to future mechanical pain.

In another test, they subjected both wild-type and mutant mice to pain induced by formalin (2% aqueous formaldehyde) injection into the paw, with and without the administration of Alda-1. The formalin-induced pain response occurs in two phases: an immediate phase (0 to 10 min) and a more sustained phase 2. In the first phase, the flinching and licking behavior showed no difference between wild-type and mutant mice (Figure S6A of Zambelli). But Alda-1 treatment significantly decreased by ~60% the early second phase pain response (10 to 40 minutes) for both the wild-type and mutant mice (Figure S6B of Zambelli). These tests for pain utilized compounds (acetaldehyde and formaldehyde) that are known to directly activate nociceptive neurons via the TRPA1 calcium channel [Bang, 2007; McNamara, 2007].

Zambelli et al. conducted several other tests that involved pain that was due to the inflammation that was caused by an injection of carrageenan (a linear sulfated polysaccharide that is known to induce mechanical and cold hypersensitivity due to localized inflammation [Li, 2012]). A treatment protocol was developed involving a "baseline test", a pre-treatment with Alda-1 (or vehicle), treatment with carrageenan, two more treatments with Alda-1 (or vehicle) spaced 2 hours apart, and then a "final test" 3 hours after the carrageenan treatment (FIG. 2A of Zambelli).

This protocol was first used to compare the relative mechanical pain sensitivity (using von Frey hairs) of the two types of mice (treated with vehicle, not Alda-1). There was no difference in the "baseline test" nociceptive behavior between the wild-type and ALDH2*1/*2 mice (using an "up-down" measurement of mechanical pain sensitivity), however in the "final test" the wild-type mice had become ~2.4 times more sensitive to mechanical pain and the ALDH2*1/*2 had become ~21 times more sensitive (FIG. 2B of Zambelli). The carrageenan-induced inflammation had increased the mechanical pain sensitivity of the ALDH2*1/*2 mice by a factor of ~9 compared to the wild-type mice.

In a separate subset of mice, they then used the same treatment protocol to determine the effect of treatment with Alda-1. At the 1.2 g stimulus level, the ALDH2*1/*2 mice were ~3× more sensitive to pain than the wild-type mice. But with the Alda-1 treatment, they were actually ~30% less sensitive than the wild-type mice without treatment (FIG. 2E of Zambelli). In other words, with Alda-1 treatment, the ALLDH2*1/*2 mice were no longer hypersensitive to mechanical pain (relative to untreated wild-type mice).

In summary, these animal tests show that in the absence of aldehyde exposure or inflammation, there is not a significant difference in pain response between wild-type and ALDH-2*1/*2 mice. Furthermore, the significant effect of low ALDH activity was shown to be the aldehyde-induced sensitization of the animal to mechanical pain. There was not a sensitization to the initial treatment of the aldehyde itself, which always produced an identical response in these tests. (See also the U.S. Pat. No. 9,545,393 which was granted to Zambelli et al.)

In terms of my Chinese acquaintance, the symptoms from her (presumed) inheritance of ALDH2*1/*2 fit the pattern. Her suffering from mechanical pain (and pain from cold temperatures, see below) was not a direct effect from aldehydes themselves, but an indirect effect of the pain sensitization that is induced by aldehydes (e.g. as produced by chronic low-level inflammation, see below).

3.2.4 Aldehydes are Sensed by Specific Nociceptive Neurons.

Painful chemical signals are detected by the peripheral terminals of a subset of primary sensory neurons ("nociceptor fibers"). Ion channel proteins located in the plasma membrane of these neurons transform the chemical signals into electrical potentials. For acetylaldehyde (and also other aldehydes) the specific sensory protein has been determined to be "Transient Receptor Protein μl" (TRPA1) [Bang, 2007], [Baraldi, 2010].

TRPA1 is a member of the TRP family of non-specific cation channel proteins that are commonly found in sensory neurons. For comparison, another example in the TRP family is the TRPV1 protein which is sensitive to noxious heat (>42 degrees C.), some pungent compounds like capsaicin (which makes chili peppers taste hot), and some specific lipids. Interestingly, nearly every nociceptive neuron that expresses TRPA1 also expresses TRPV1. Furthermore, TRPA1 and TRPV1 share some common agonists and are known to interact. However, in the interest of brevity and conciseness, I will concentrate on TRPA1 (the sensor for aldehydes), mechanical pain hypersensitivity, and cold pain hypersensitivity.

Noxious compounds including allicin (from garlic), allyl isothiocyanate (AITC, from mustard), cinnamaldehyde (from cinnamon), and α,β-unsaturated aldehydes, respectively, elicit acute pain and neurogenic inflammation by activating TRPA1 [Hinman, 2006, which is hereby included by reference]. Each of these compounds is capable of forming covalent adducts with thiols (such as cysteine) and to a lesser extent primary amines (such as lysine) (FIG. 1 of Hinman, 2006). It has been found that this variety of structurally distinct compounds activate TRPA1 primarily involving covalent modification of three specific cysteines (and a specific lysine) located within the intercellular N-terminal domain of the channel (FIG. 7, from FIG. 3a of Hinman).

See figures FIG. 3A to FIG. 3H and FIG. 4A to FIG. 4E, which illustrate various compounds that are known TRPA1 agonists, with a dotted-line circle drawn around the reactive group of each molecule. Note that many of these compounds have an oxygen atom that is double bonded to a carbon (e.g. they are "carbonyls") that is part of their reactive group. Many of these carbonyls are also aldehydes. Formaldehyde (FIG. 3F) is a simple aldehyde while the other aldehydes (FIGS. 3A, 3D, and 3H) are "α,β-unsaturated aldehydes" due to a nearby (—C=C) carbon to carbon double bond. The others include "α,β-unsaturated carbonyls" (FIG. 3G and FIGS. 4A, 4B, 4C and 4E). It is the electrophilic nature of these compounds that makes them reactive with the sensitive cysteines (and to a lesser extent, the sensitive lysine) of the TRPA1 protein.

Neurons from TRPA1-null mice do not respond the cysteine-modifying compounds (FIG. 2e of Hinman). To identify the cysteines within the TRPA1 protein that are necessary for detecting these agonists, they generated a series of cysteine-to-serine or -alanine substitutions at 13 of the 21 positions that are invariant among human, rat, and mouse TRPA1 sequences. Replacement of 10 cysteine residues had little or no effect on channel function: however, substitutions at three closely spaced positions (C619, C639, and C663), located within the cytoplasmic N terminus (FIG. 7, from FIG. 3a of Hinman)) resulted in partial, but significant and cumulative, decreases in electrophile-evoked responses. The resulting triple mutant (TRPA1-3C) exhibited pharmacological properties consistent with the specific ablation of cysteine-modification mediated channel gating (FIG. 3b of Hinman).

Interestingly, even though the TRPA1-3C mutant had a significantly decreased response, there was still present a weaker and slower response to electrophilic agonists (e.g. a factor of $\frac{1}{10}$ in the dose-response curve) (FIG. 4a of Hinman). Furthermore, this activity was not reversible under washout (FIG. 4b of Hinman), indicating that it was not due to the modification of a cysteine. This led to the investigation of whether the residual response could be due to the irreversible modification of lysines. They found that replacing lysine-708 with arginine (K708R) rendered the TRPA1-3C mutant completely insensitive to the agonist (FIG. 4c of Hinman).

3.2.5 Physical Structure of the TRPA1 Channel.

In order to understand the properties of the TRPA1 channel, it is useful to have a basic understanding of its physical structure. The channel is a tetramer formed from 4 symmetrically interconnected units of the TRPA1 protein. Due to the difficulty of obtaining XRay images of membrane-bound proteins, no detailed atomic level structure has been produced. However, using single-particle electron cryo-microscopy the structure of full-length human TRPA1 was determined to ~4 angstrom resolution, approximately the size of a calcium atom [Paulsen, 2015, which is hereby included by reference]. The side view density map image (FIG. 1c of Paulsen) is labeled to show the extracellular, membrane bound and intracellular regions of the channel along with the corresponding side view which clearly shows its tetrameric symmetry.

When viewed as a ribbon diagram (FIG. 1e of Paulsen), the side view clearly shows the alpha-helices in the membrane bound region (a total of 24) and the "ankyrin repeats" (a total of 4) that dominate the cytoplasmic portion of the channel. The top view focuses on the upper gate (a 7 angstrom diameter hole in the center) while the bottom view focuses on the lower gate (a 6 angstrom diameter hole in the center). Note that this is for an AITC-treated sample, so the channel is in a partially opened state. A key point is that there are two flow restriction points in the channel, and that their diameter is comparable to the diameter of hydrated calcium atoms.

In the more detailed reconstruction of the ion permeation pathway (FIG. 6a of Paulsen), the constriction points can be seen, along with the labels "D915" for the upper constriction and "V961" for the lower constriction. A plot of the pore radius variations along the pore axis with the channel in its closed state is shown in FIG. 6 (from FIG. 6b of Paulsen). The "selectivity filter" has a pore radius of ~2 angstroms and the "lower gate" pore radius is ~1.5 angstroms. These are both smaller than the diameter of a calcium atom (~4 angstroms).

Furthermore, two cross sectional views of the channel (FIG. 1e of Paulsen), taken at each constriction point, clearly show that the upper gate is within the membrane region (and presumably controlled by the alpha helices) and that the lower gate is at the transition to the cytoplasmic region (and presumably controlled, or at least influenced, by the ankyrin repeats which are known to have mechanical spring-like properties and to bend under the influence calcium and ATP) [Gaudet, 2008].

One limitation of this microscopy is that it not able to resolve features that are positionally unstable. There are actually four more ankyrin repeats at the bottom of the channel which surround the four ankyrin repeats that were resolved. These can be seen as a faint ring (FIG. 1a of Paulsen). Although these have been shown to be involved in mechanical sheer detection and in cold temperature detection, they are unlikely to be the direct mediators for opening and closing the channel gates. Optical images produced by a scintillator-based CMOS camera (at 28 angstrom resolution) show that these form an almost independent ring at the bottom of the channel (Extended Data FIG. 2e of Paulsen).

3.2.6 Fully Activated TRPA1 Produces a Transient Current.

When TRPA1 is exposed to an agonist (e.g. AITC) and a physiological concentration of $Ca^{2+}$ is present on the extracellular side of the membrane (e.g. in the mM range), an amount current flows through the channel that depends on the membrane potential (voltage) and the duration of time. See FIG. 5A (which is derived from FIG. 7C of Banke, 2010]). When the AITC agonist is first applied, the amount of current increases with time, and the rate of increase also increases with time until a peak is reached (in 30 seconds), after which the current decreases, in a curved descent (e.g. for 60 seconds). This indicates a gradual opening of the channel that speeds-up until the channel is completely open. This is followed by the closing of the channel and a refractory period during which the channel does not respond to stimulus (e.g. the second time that AITC is applied in FIG. 5A). The refractory period for an individual TRPA1 channel can be 20 minutes [Wang, 2008].

More information on the fully open state of the channel is shown in FIG. 5B (which is derived from FIG. 7E of [Banke, 2010]). Every 5 seconds, the conductivity (current vs. voltage) was measured (e.g. at the "spikes" visible in FIG. 5A) to determine how selective the channel was at passing primarily cations. At time 1 (labeled "1" in both parts of FIG. 5), the channel is completely closed (no current at any voltage). At time 2, the channel is highly rectifying (no significant current for negative voltages, showing a high selectivity for cations). By time 3, it now also conducts significantly for negative voltages, showing less selectivity. This is due to the opening up of the upper gate (the "selectivity filter") and of the lower gate. While formerly these only passed positively charged atoms, now they can also pass negatively charged atoms, or even entire small molecules.

Note that the "transient" nature of the channel has the effect of preventing a toxic calcium overload within the cell. Also, this localized "pulse" of high calcium concentration can trigger localized neurotransmitter release from the sensory neuron [Koivisto, 2014].

3.2.7 The Role of the TRPA1 Channel in Hypersensitivity.

The TRPA1 channel is expressed particularly by nociceptive primary afferent neurons. At peripheral terminal of the neuron, TRPA1 channels perform the transduction of potentially harmful stimuli into electric signals. But at the other end of these neurons, TRPA1 channels are also located at the neuron's central terminal (at the "spinal dorsal horn") where they modulate neurotransmitter release. The TRPA1 channels at the central terminal of these neurons, and at the central terminal of other primary afferent neurons that terminate nearby in the same spinal dorsal horn, serve as inputs which can sensitize all of these neurons to further stimulation [Wei, 2010].

For male rats, the topical application of mustard oil on the skin of the ankle subsequently produced a strong hypersensitivity to mechanical stimulation (measured by using von Frey hairs to apply a calibrated force at a point on the skin) at the center of the treatment site ("site of primary hyperalgesia"). There was also a strong hypersensitivity to mechanical stimulation at a site 2 cm away from this ("site of secondary hyperalgesia"). Pre-treatment with a TRPA1 inhibitor ("CHEM") at the mustard oil treatment site reduced the primary hyperalgesia from the mustard oil (by ~25% at 10 min, ~33% at 30 min, FIG. 3A of Wei). Interestingly, pre-treatment with CHEM via a catheter to the spinal cord (instead of at the mustard oil site) dramatically decreased the secondary hyperalgesia (by ~70% at 10 min, ~80% at 30 min, FIG. 3C of Wei). They conclude that the spinally located TRPA1 channels play an important role in the development and maintenance of topical mustard oil-induced hyperalgesia, after being originally induced by the activation of a cutaneous TRPA1 channel. (In other words, the activation of a TRPA1 channel at the cutaneous end of the neuron caused a (TRPA1 based) interaction with other sensory neurons at the central end of this neuron that in turn sensitized their far away cutaneous TRPA1 channels.)

A ganglion is a group of nerve cell bodies. The sensory neurons from a specific area of skin are associated with a specific dorsal root ganglion, located at the spinal cord. The "mapping" of skin areas to specific dorsal root ganglia is defined as the "dermatome". One early model for the development of secondary hyperalgesia (e.g. as seen from mustard oil at 10 min) was that microglia (or astrocytes) are attracted to the affected dorsal root ganglion and become activated, causing localized inflammation that sensitizes the central end of the nociceptive neuron.

However, researchers have failed to find activated microglia in the spinal cord over a similar time course as the secondary hyperalgesia following nociceptor activation with a chemical irritant (topical mustard oil treatment) [McMahon, 2005]. This is not to say that spinal microglia never become activated, it's just that they are not the cause of the rapid onset of secondary hyperalgesia that is observed in these experiments. Over a longer time period (hours to days later), the activation of immune system cells such as microglia, astrocytes, and neutrophils can produce continued hyperalgesia during the healing period and possibly beyond (e.g. in the maintenance of chronic pain).

Nociceptive neurons are known to release neurotransmitters, neuroactive peptides, and other neuroactive molecules when they are activated. For example, glutamate is the neurotransmitter that is released at the synaptic connection from the nociceptive neuron to the spinal cord neuron that propagates the painful signal to the brain. Glutamate is known to also be released from primary afferent terminals after formalin injection. Extracellular glutamate is an agonist for nociceptor neurons that express TRPA1 (and therefore also TRPV1) and is believed to contribute to the development of persistent pain states [McMahon, 2005].

The neuroactive peptides include "calcitonin gene-related peptide" (CGRP) which is a potent vasodilator, and "Substance P" (SP) which stimulates various cells to release pro-inflammatory cytokines (e.g. IL-1, IL-2, and TNF) which can attract and activate microglia and astrocytes. Therefore, the initial inflammation (neurogenic inflammation) can be due to these neuropeptides, while subsequent inflammation can be due to an induced, localized, immune response. It has been experimentally verified that the TRPA1 agonists (e.g. 4-HNE or cinnamaldehyde) evoke the release of both CGRP and SP, from both the central endings and the peripheral endings of sensory nerves that express TRPA1 [Trevisani, 2007], thereby starting an inflammation that may later be sustained due to an immune response.

The primary hyperalgesia can be due to these neuroactive peptides. But the essential mechanism for the rapid development of secondary hyperalgesia in nociceptor neurons that express TRPA1 has been discovered to be the intracellular calcium-induced release of hydrogen peroxide (a TRPA1 agonist) from activated sensory neurons. The resulting $H_2O_2$ is membrane permeable and readily diffuses within biological tissues, activating nearby nociceptor neurons.

A detailed study determined that TRPA1 is responsible for detecting noxious $H_2O_2$ as pain [Sawada, 2008, which is hereby included by reference]. This was followed by another detailed study that determined that $H_2O_2$ is both produced by the activation of nociceptor neurons that express TRPA1 and also detected by other TRPA1 expressing nociceptor neurons that are co-located with them in the dorsal horn, thereby mediating inflammatory hyperalgesia [Keeble, 2009, which is hereby included by reference]. Their findings are listed below.

[Sawada 2008] Using HEK 293 cells transfected with mouse TRPA1:
- $H_2O_2$ treatment caused significant intracellular $Ca^{2+}$ due to $Ca^{2+}$ influx (FIG. 1 of Sawada).
- Adding catalase (which scavenges $H_2O_2$) abolished the $H_2O_2$-induced $Ca^{2+}$ increase (FIG. 2 of Sawada).
- Alternatively, adding camphor (which specifically inhibits TRPA1) prevents the $H_2O_2$-induced $Ca^{2+}$ increase (FIG. 2 of Sawada).
- Using patch-clamp recordings, is was confirmed that the $H_2O_2$-invoked current was through "non-selective cation channels" (i.e. the TRPA1 channels) (FIG. 3 of Sawada).
- Using an excised membrane patch from TRPA1-expressing cells:
  - Cell-free inside-out recordings from a single $H_2O_2$ activated TRPA1 channel show that the conductance of the open channel is exactly the same as when channel is activated by the TRPA1 agonist AITC (FIG. 3 of Sawada). These cell-free inside-out recordings indicate that the activation of the TRPA1 channel requires no other intracellular components.

Using HEK 293 cells transfected with mouse TRPA1:
- The membrane-permeable cysteine-reducing agent dithiothreitol ("DTT") markedly decreased the response to $H_2O_2$ thereby confirming the role of cysteine oxidation in the activation of TRPA1 (FIG. 5 of Sawada).
- The membrane-permeable cysteine-oxidizing reagent 2,2'-dipyridyl disulfide increased intracellular $Ca^{2+}$ in a dose-dependent manner, thereby further confirming the role of cysteine oxidation in the activation of TRPA1 (FIG. 5 of Sawada).
- The subset of neurons that are activated by $H_2O_2$ are also activated by AITC. Considering that AITC is a TRPA1-specific agonist, this confirms that $H_2O_2$ activates TRPA1-expressing sensory neurons in vivo (FIG. 6 of Sawada).

[Keeble, 2009] Using $H_2O_2$ injections into one mouse hind paw:
- At 20 min, the increase in mechanical hyperalgesia is dose-dependent (FIG. 1 of Keeble). The half-maximal dose was chosen for the following tests.
- At 20 min, in addition to the mechanical hyperalgesia, thermal hyperalgesia and nociceptive behavior are observed (FIG. 1 of Keeble).
- At 2 hours (to allow inflammation to have developed), dorsal horn sections show a significantly increased number of c-fos positive neurons (a marker for recent neuronal activity) on the injected side (e.g. the side connected to the injected hind paw), but not on the uninjected side (FIG. 2 of Keeble).

Using carrageenan injections into one mouse hind paw:
- Note that carrageenan, a sulfated polysaccharide, is not a direct agonist of TRP channels. It is used to cause a strong immune response and painful localized inflammation. Measured at 4 hours, there was significantly more $H_2O_2$ in homogenates of the carrageenan-treated paw compared to the opposite (saline treated) paw, indicating that $H_2O_2$ is produced endogenously in the carrageenan-treated paw (FIG. 3 of Keeble).
- In order to remove superoxide and $H_2O_2$ from the system, super oxide dismutase (SOD) and catalase were co-injected along with the carrageenan. Measured at 4 hours, the SOD and catalase ameliorated both the mechanical and the thermal hyperalgesia (FIG. 4 of Keeble).

Using $H_2O_2$ injections into the mouse hind paw: To determine the role of TRPV1 (one of the types of TRP channels that produce pain from excessive heat, as opposed to TRPA1 which produces pain from mechanical stimulus or from excessive cold), the responses of wild-type vs. TRPV1 knockout mice to $H_2O_2$ injections were compared, at multiple time points. For mechanical hyperalgesia, the responses were the same for both types of mice, with significant sensitization at all time points (20 min, 1 h, 4 h, and 24 h). But for high heat hyperalgesia, the TRPV1 knockout mice had less sensitization at 1 h, 4 h, and especially 24 h (FIG. 5 of Keeble). (This demonstrates the crosstalk between the sensitization provided by TRPA1 and the thermal response of TRPV1. TRPA1 may also hypersensitize other nociceptors—because intracellular calcium is additive.)

At 4 hours, the $H_2O_2$ injection caused a significant increase in MPO activity in that paw, an indicator of neutrophil accumulation. However, no increase in MPO activity was detected at the 20 min time point.

Taken all together, these experiments provide compelling evidence that intracellular calcium-induced $H_2O_2$ is a significant sensitizer for TRPA1 channels, and that TRPA1 is largely responsible for mechanical hyperalgesia.

A review article [Brookes, 2004] describes various ways that a high concentration of $Ca^{2+}$ can cause mitochondria to produce excessive $H_2O_2$. The simplest of these is that a high level of calcium activates nitric oxide synthase and the subsequent nitric oxide inhibits respiration at "complex IV", resulting in superoxide production. The superoxide is then converted to $H_2O_2$ by superoxide dismutase.

3.2.8 The Role of TRPA1 in Cold Hypersensitivity

There was some controversy over the role of TRPA1 in cold pain, with some groups reporting that cold directly activates TRPA1, and others not being able to replicate these results. However, it was discovered that, when pre-treated with a chemical agonist (even at a low level), TRPA1 can reliably be activated by cold [del Camino, 2010]. For isolated TRPA1 positive neurons, patch-clamp recordings show that exposure to a low level of the aldehyde 4-HNE produced a low level of current flow at 25 degrees C., that was potentiated by a factor of 3 by lowering the temperature to 10 degrees (FIG. 4 of del Camino). They also performed an experiment with mice that showed that the injection into the hind paws of a low dose of 4-HNE (that produced no pain response at room temperature) significantly increased the pain response to being placed on a zero degree cold plate. The time to "first jump" for "vehicle treated" mice was 125 seconds, but for the 4-HNE treated mice it was only 20 seconds (FIG. 5 of del Camino).

In other words, without being sensitized, TRPA1 does not produce cold pain. Cold feels cold, but not painful. But even a low level of a chemical agonist can sensitize TRPA1 to cold.

Interestingly, TRPA1 is not needed at all for normal tactile perception, normal heat perception and the normal initial pain response. The role of TRPA1 appears to exclusively be the sensitization of mechanical pain and of cold pain [Bautista 2013].

3.2.9 Involvement of the Immune System in Chronic Pain

Inflammation need not involve the immune system. The hallmarks of inflammation (pain, redness of skin, . . . ) can be produced by neurogenic inflammation. But sustained inflammation (weeks, months, years, . . . ) seems to always involve a corresponding immune response. Activated immune-response cells, including microglia, astrocytes, neutrophils, and even fibroblasts, emit reactive oxygen species (ROS, e.g. hydrogen peroxide, superoxide) reactive nitrogen species (RNS, e.g. nitric oxide) and even peroxynitrite (formed from superoxide+ nitric oxide). These all will peroxidise membrane lipids, and each peroxidised lipid will each eventually spontaneously split into two aldehydes (one free and one membrane bound). Thanks to phospholipase A, the membrane bound aldehyde will also eventually become free.

The role of the immune response in TRPA1 activation and subsequent disease states is detailed in the paper "TRPA1: A Gatekeeper of Inflammation" [Bautista 2013]. Chronic inflammation can lead to a host of diseases, including asthma, itch, rheumatoid arthritis, and colitis.

3.2.10 Lipid Peroxidation Leads to Aldehyde Formation

The steps in aldehyde formation from fatty acids are further illustrated in FIG. 11. For purpose of this example, a simple omega-6 unsaturated fatty acid with 10 carbons and one double bond (10:1ω6) is shown in FIG. 11A. For a fatty acid, carbons are normally counted from the carboxyl end, but the "omega" count starts from the far end. Counting from the omega end, the double bond starts at carbon 6 (this will end up determining the length of the aldehyde product shown in FIG. 11C). Because of the double bond, this fatty is subject to peroxidation from ROS (FIG. 11B) at either carbon 5 (illustrated) or at carbon 4 (the other end of the double bond). In either case, the peroxidized fatty acid can spontaneously split between carbons 4 and 5, with an oxygen and a hydrogen attached to the terminal carbon of each product. The simple aldehyde (FIG. 11C) is hexanal (with 6 carbons, thanks to having produced from an omega 6 fatty acid), while the other aldehyde (succinic semialdehyde, FIG. 11D) retains the carboxyl group, and its length is 4 carbons (10 minus 6). If this fatty acid had been part of a phospholipid (e.g. part of a cellular membrane), the hexanal would float away (initially within the lipid membrane) while the other half would remain bound to the membrane (unless it becomes released by a phospholipase).

4. Summary of the Invention

Nociceptive neurons that express the TRPA1 non-selective cation channel become sensitized to mechanical stress and cold temperatures when specific cysteine and lysine residues of the TRPA1 protein become modified by electrophilic compounds such as aldehydes. This hyper-sensitizes pain-sensing neurons and can also produce painful sensations from stimulus that would not otherwise cause pain. The invention uses low molecular weight lipophilic mercaptans to scavenge the aldehydes and other noxious molecules that could otherwise activate TRPA1, thereby reducing this unnecessary pain.

In one aspect, the present disclosure provides a method to treat a subject with pain sensitization, the method comprising orally administering to the subject an effective amount of a lipophilic mercaptan to decrease protein-aldehyde adducts of TPRA1 in the subject. According to the present disclosure, when administered in an effective amount, the lipophilic mercaptan reacts with aldehydes within the lipid membranes of said animal, said aldehydes being in the form of an aldehyde and/or in the form of protein-aldehyde adduct(s) (including protein-aldehyde adducts of TRPA1). This produces a molecular conjugate of said lipophilic mercaptan and said aldehyde, and decreases protein-aldehyde adducts of TPRA1 directly and/or indirectly (e.g. by scavenging aldehydes). In some examples, the subject in need of treatment may be a subject with allodynia or a subject with pain hypersensitivity. Alternatively, or in addition, a subject with pain sensitization may be a subject with the ALDH2*2 allele. In still further examples, a subject with pain sensitization may be a subject that is/was responsive to gabapentin (or other aldehyde scavenger) but is in need of further treatment or alternative treatment due to side effects or limited efficacy.

In another aspect, the present disclosure provides a method to treat a subject with pain hypersensitivity, the method comprising orally administering to the subject an effective amount of a lipophilic mercaptan to decrease protein-aldehyde adducts of TPRA1 in the subject. According to the present disclosure, when administered in an effective amount, the lipophilic mercaptan reacts with aldehydes within the lipid membranes of said animal, said aldehydes being in the form of an aldehyde and/or in the form of protein-aldehyde adduct(s) (including protein-aldehyde adducts of TRPA1). This produces a molecular conjugate of said lipophilic mercaptan and said aldehyde, and decreases protein-aldehyde adducts of TPRA1 directly and/or indirectly (e.g. by scavenging aldehydes). In some examples, a subject with pain hypersensitivity has been diagnosed with chronic pain. Alternatively, or in addition, a subject with pain hypersensitivity may be a subject with the ALDH2*2 allele. In still further examples, a subject with pain hypersensitivity may be a subject that is/was responsive to gabapentin (or other aldehyde scavenger) but is in need of further treatment or alternative treatment due to side effects or limited efficacy.

In another aspect, the present disclosure provides a method to treat pain hypersensitivity in a subject in need thereof, the method comprising orally administering to the subject an effective amount of a lipophilic mercaptan; thereby decreasing the subject's pain hypersensitivity. In some examples, a subject with pain hypersensitivity has been diagnosed with chronic pain. Alternatively, or in addition, a subject with pain hypersensitivity may be a subject with the ALDH2*2 allele. In still further examples, a subject with pain hypersensitivity may be a subject that is/was responsive to gabapentin (or other aldehyde scavenger) but is in need of further treatment or alternative treatment due to side effects or limited efficacy.

In another aspect, the present disclosure provides a method to treat pain in a subject with an ALDH2*2 allele, the method comprising orally administering to the subject an effective amount of a lipophilic mercaptan. Subjects with an ALDH2*2 allele have an increased risk of developing pain hypersensitivity than subjects without ALDH2*2 allele. In some examples, a subject with an ALDH2*2 allele does not have pain sensitivity. In other examples, a subject with an ALDH2*2 allele has pain sensitivity.

In another aspect, the present disclosure provides a method to treat pain in a subject that is responsive (or was previously responsive) to gabapentin (or other aldehyde scavenger) but is in need of further treatment or an alternative treatment due to side effects or limited efficacy, the method comprising orally administering to the subject an effective amount of a lipophilic mercaptan. In some examples, the subject does not have pain sensitivity. In other examples, the subject has pain sensitivity.

The treatment can be administered as a dietary supplement, without the negative side effects that are a common feature of currently available aldehyde scavenging drugs. Furthermore, the treatment does not significantly alter basil tactile and pain detection, which serve an important protective function. Non-limiting examples of suitable lipophilic mercaptans include allyl mercaptan (a metabolite from garlic) and propyl mercaptan (a metabolite from onion), allowing these already FDA approved garlic and onion derived compounds to be used for the dietary supplements.

Non-dietary mercaptans are also disclosed, which are suitable for development as drugs. The procedures for drug development are known within the art, and necessarily require clinical trials before FDA approval is obtained.

5. BRIEF DESCRIPTION OF THE DRAWINGS

The patent or application file contains at least one drawing executed in color. Copies of this patent or patent application with color drawing(s) will be provided by the Office by request and payment of the necessary fee.

FIGS. 3A, 3B, 3C, 3D, 3E, 3F, 3G, and 3H show various compounds that are TRPA1 agonists.

FIGS. 4A, 4B, 4C, 4D and 4E show additional compounds that are TRPA1 agonists.

Figure 5A:
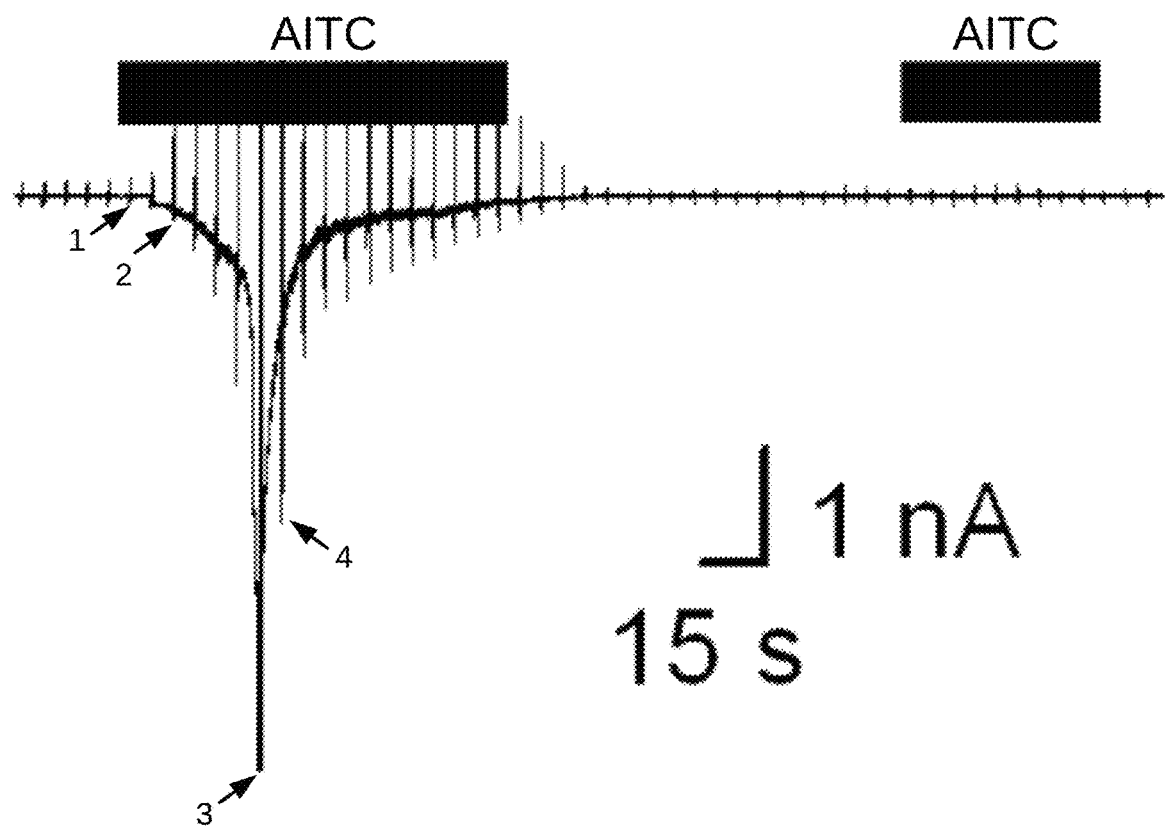
Figure 5B:
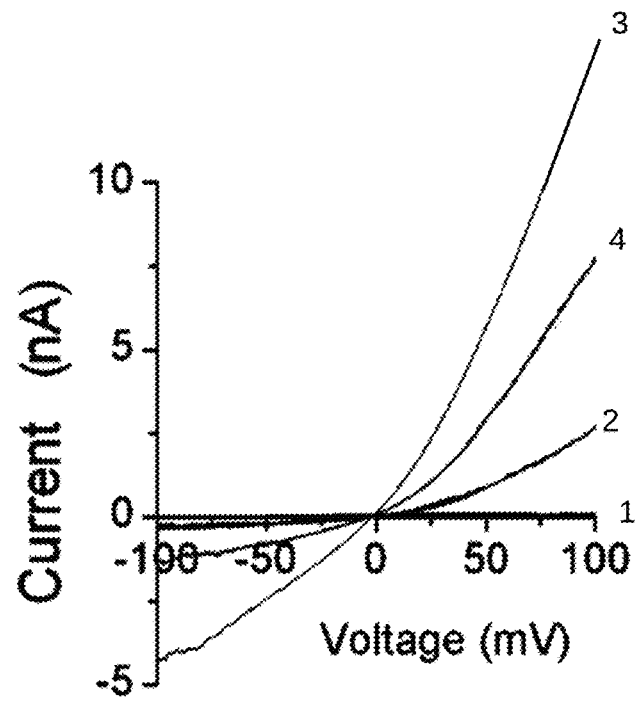
Figure 7:
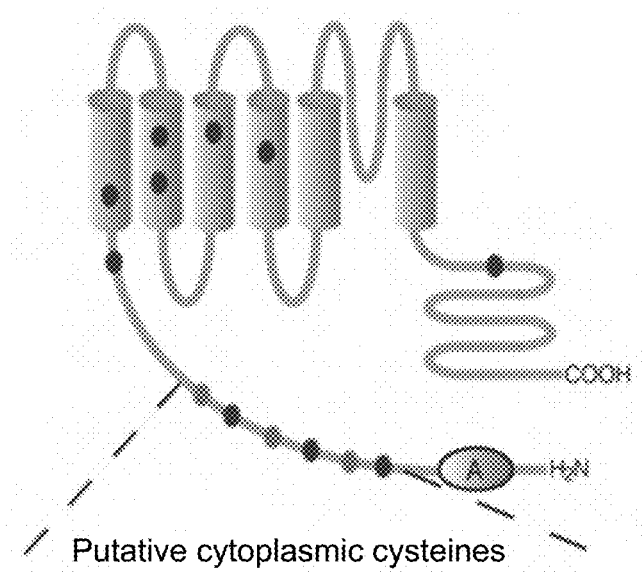

FIGS. 5A and 5B show the conductance of a TRPA1 channel (from FIG. 7 of Banke, 2010]).

Figure 6:
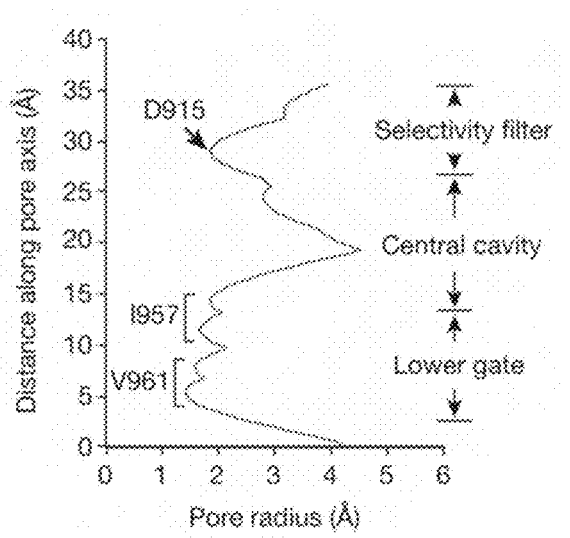

FIG. 6 shows the pore radius of a closed TRPA1 channel along the pore axis (from FIG. 6b of [Paulsen, 2015]).

Figure 3A:
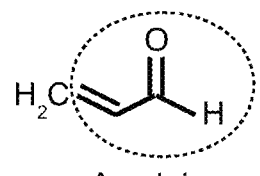
Figure 3B:
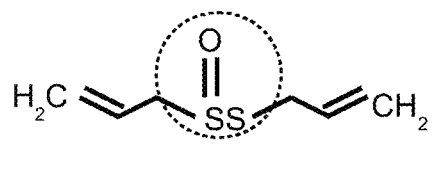
Figure 3C:
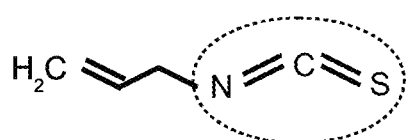
Figure 3D:
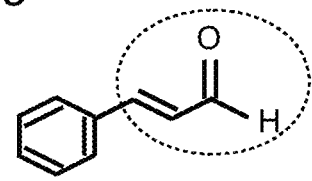
Figure 3E:
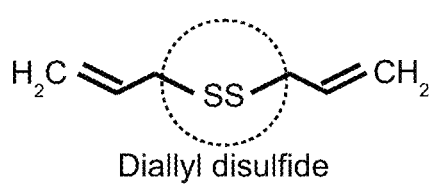
Figure 3F:
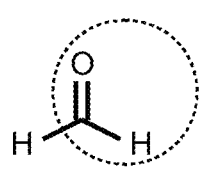
Figure 3G:
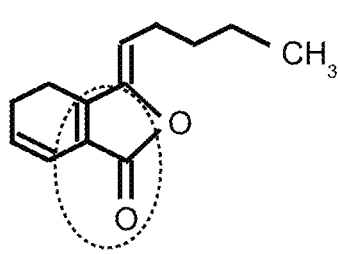
Figure 3H:
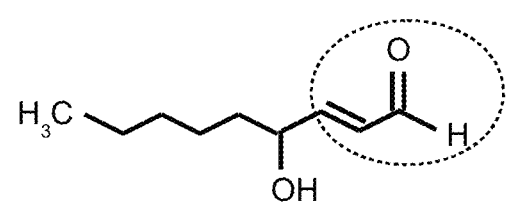
Figure 4A:
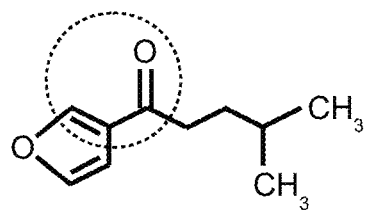
Figure 4B:
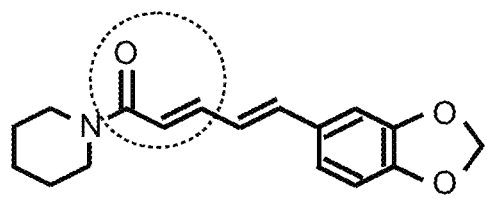
Figure 4C:
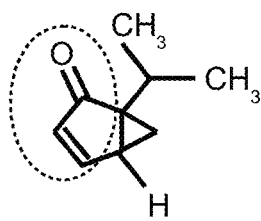
Figure 4D:
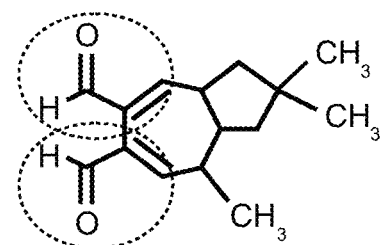
Figure 4E:
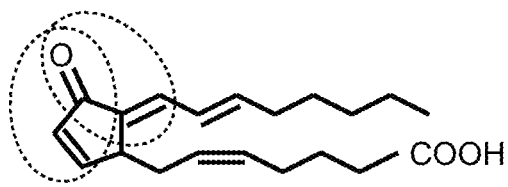

FIG. 7 shows an early model for the structure of TRPA1 (from FIG. 3a of [Hinman, 2006]).

Figure 8A:
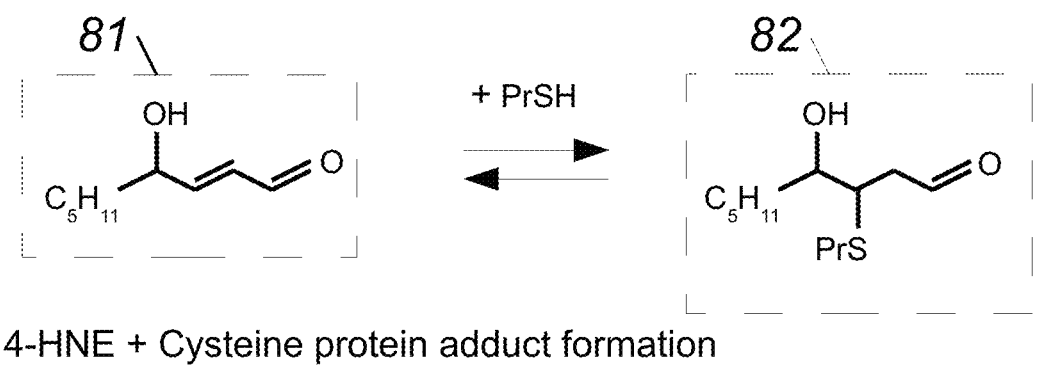
Figure 8B:
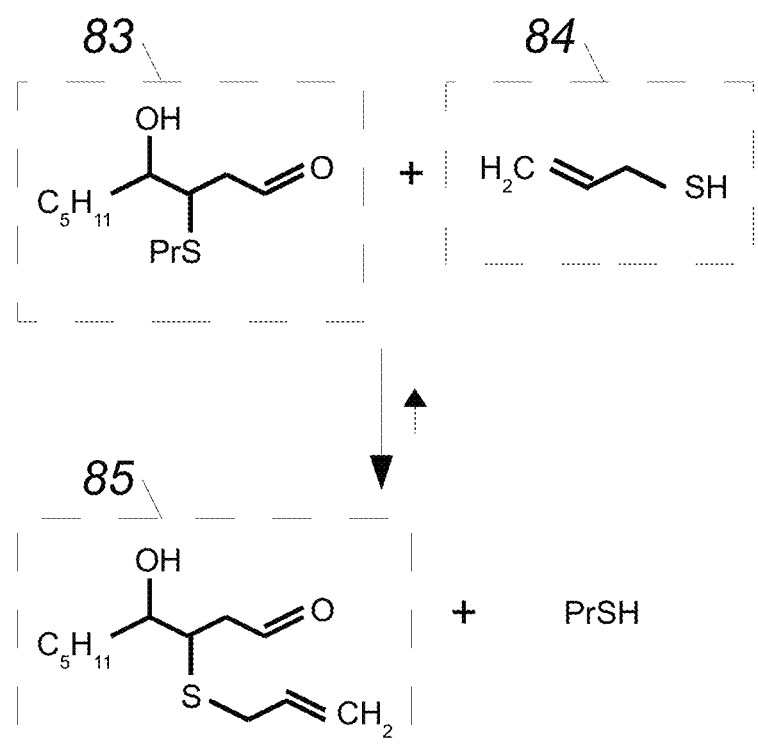

FIGS. 8A and 8B show aldehyde-cysteine protein adduct formation and repair.

Figure 9A:
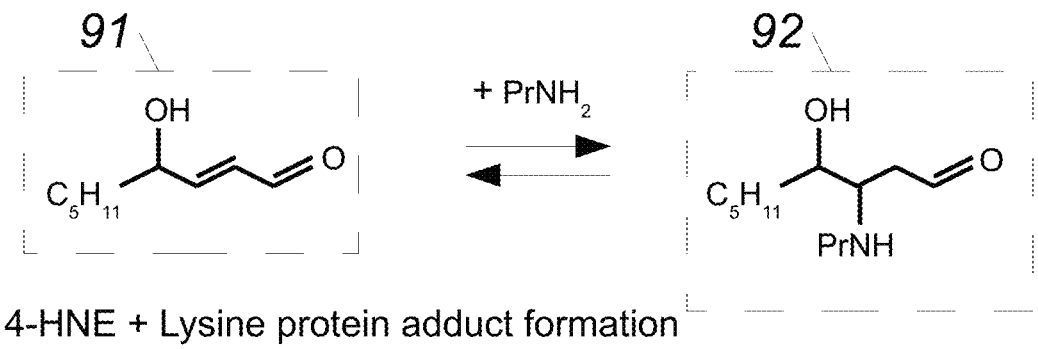
Figure 9B:
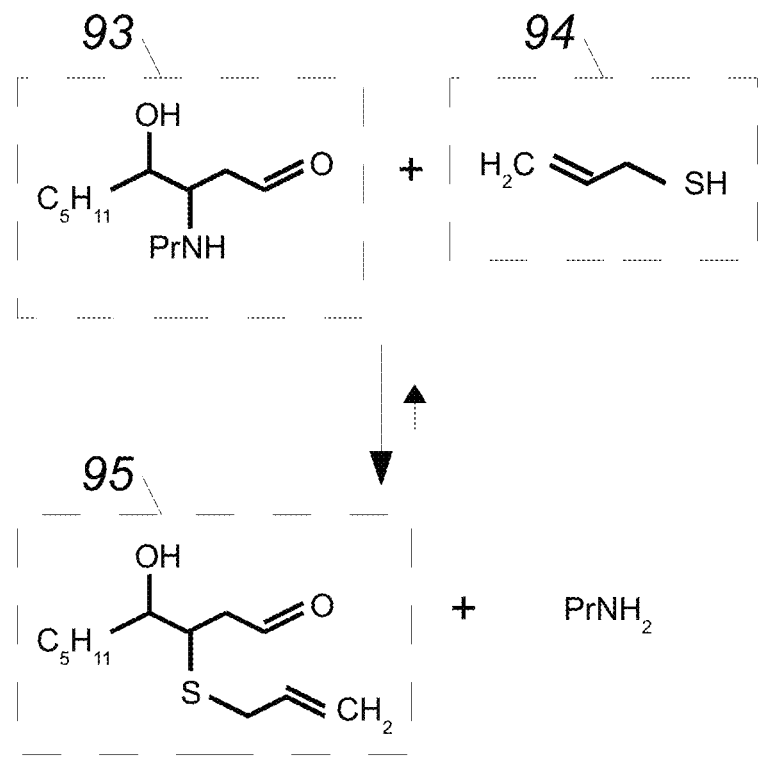

FIGS. 9A and 9B show aldehyde-lysine protein adduct formation and repair.

Figure 10:
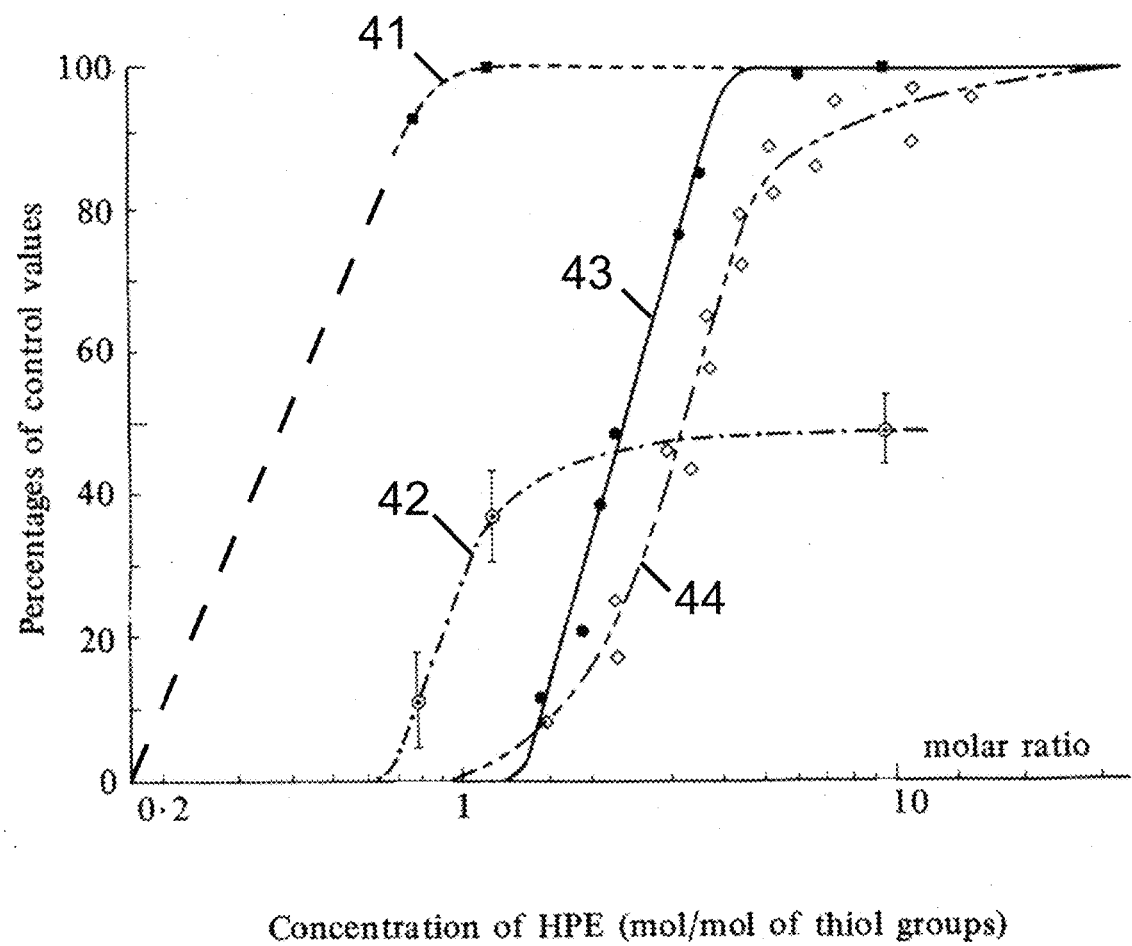
Figure 11A:
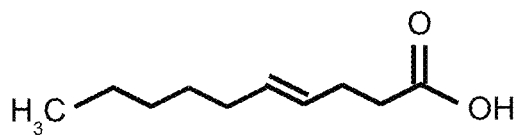
Figure 11B:
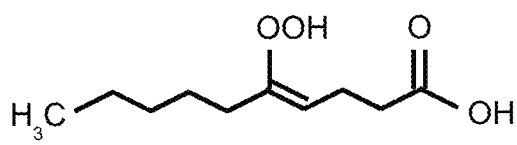
Figure 11C:
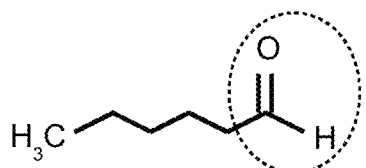
Figure 11D:
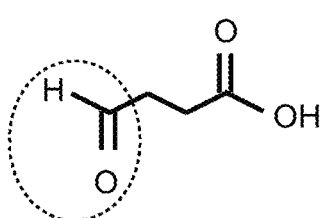

FIG. 10 shows aldehyde-induced depletion of thiol groups (from FIG. 3.10 of [Schauenstein, 1977]).

FIGS. 11A, 11B, 11C and 11D show compounds associated with lipid peroxidation and subsequent aldehyde formation.

FIGS. 12A, 12B, 12C, 12D, 12E, and 12F show other compounds of interest.

Figure 13A:
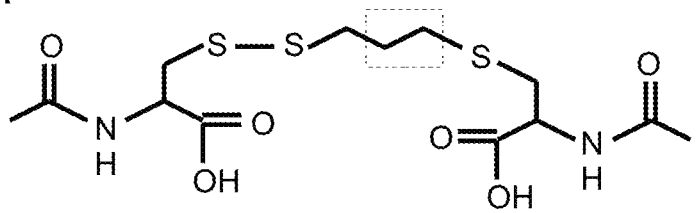
Figure 13B:
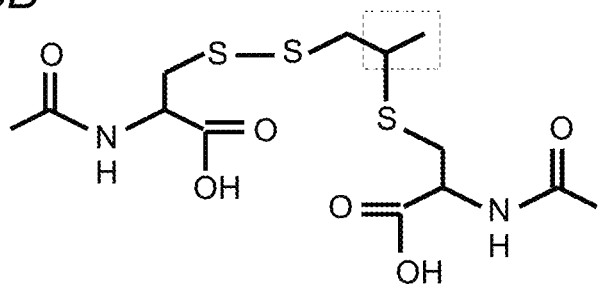
Figure 13C:
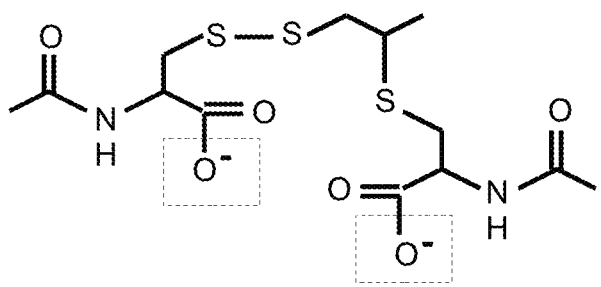

FIGS. 13A, 13B, and 13C show other dietary supplement compounds.

6. DETAILED DESCRIPTION OF THE INVENTION

6.1 The Backstory

6.1.1 The Dietary Supplement

U.S. Pat. No. 8,222,299 teaches and claims a broad spectrum antibiotic which also has antioxidant properties, consisting of a mercaptan that is disulfide bonded to a protein that contains cysteines. Several versions of this dietary supplement have been produced, with the first one using whey protein plus garlic oil. The most recent of these is the "Protein-Allium" capsule which is produced from 250 mg of rice protein, 48 mg of onion oil, and 88 mg of N-acetylcysteine.

6.1.2 Transglycation

Some types of sugars (e.g. glucose, fructose) can form covalent bonds with the lysine residues of proteins, a process that is called "glycation". Note that the glucose molecule in its open-loop form is a reactive aldehyde, which is how it is able to glycate proteins.

Most of the symptoms and complications from diabetes are due to protein glycation. The discovery of nonenzymatic "transglycation", by which low molecular weight thiols (e.g. glutathione) can remove the sugar moiety from a glycated protein and thereby repair the protein [Szwergold, 2005], led to the new use of my whey protein plus garlic oil supplements for preventing and treating the complications of diabetes [U.S. Pat. No. 7,678,833].

6.1.3 Advanced Glycation End Products

Glycated proteins can become crosslinked to other proteins, forming what are called Advanced Glycation End products ("AGEs"). Visually, these aggregates tend to be brown in color (e.g. the age related spots on skin). For non-diabetic people, most of the glycation is from aldehydes other than sugar. Note that the glucose molecule in its open-loop form is an aldehyde, which is how it is able to glycate proteins.

Various neurodegenerative diseases involve protein aggregates that cause neuroinflammation (and are in turn produced by neuroinflammation) [U.S. Pat. No. 9,456,999]. For Alzheimer's disease these aggregates are commonly associated with amyloid beta, while for Parkinson's the protein is alpha synuclein although other proteins also become aggregated in these diseases. Analysis of the aggregates confirms that they are AGEs, with cross links between the lysine residues of the proteins. This led to the discovery of the new use of Protein-Allium supplements for the prevention and treatment of these neurodegenerative disease (e.g. Alzheimer's [U.S. Pat. No. 9,456,999]) by preventing the formation of these toxic AGE protein aggregates.

6.1.4 Preventing and Treating ALS

A friend of mine ("BT") has a friend ("LW") who is suffering from ALS (Amyotrophic Lateral Sclerosis). She had lost the ability to stand or walk and her legs had gotten so "heavy" and sore that she could no longer "stack" them on each other while lying down. The average ALS survival from onset to death is two to four years, with patients commonly degrading from month to month.

ALS is a neurodegenerative disease involves protein aggregates, which are called "inclusions" and are commonly associated with the protein TDP-43. Analysis of the aggregates confirms that they are AGEs. LW decided to try taking the Protein-Allium dietary supplement (3 capsules per day—equal to 144 mg of onion oil) to see if it would help. After 9 weeks, the "heavyness" of her legs had decreased, her left foot had become more flexible, and her left leg muscles could feel sensation whereas they had not had sensation before taking the supplement. In the following months her condition has continued to slowly improve, on average. For example, she has occasionally been able to stand on her left leg.

6.1.5 Protein-Allium Treatment Reduces ALS-related Pain

LW writes:
In October 2016 I was diagnosed with ALS, and have been wheelchair-bound ever since. One of my early symptoms was a "numbness" pain in my legs. For relief of this pain, NSAIDs+ OxyContin (15 mg) were prescribed.
Now I am taking Protein-Allium. This has helped a whole lot, such that I don't take NSAIDs or OxyContin anymore. The only remedy I use besides Protein-Allium is a spray called "Stop the Pain" whose main ingredient is menthol.

6.1.6 Protein-Allium Treatment Decreases Neuropathic Pain

A friend of LW (who I will call "MY") decided to try the Protein-Allium supplement to see if it could treat her neuropathic pain or her pain from adenomyosis. MY is of Chinese descent and may have the ALDH2*2 mutation that is common in this population.
MY writes:
For the last eleven years, I've been suffering from two types of chronic pain: neuropathy in my shoulder; and uterine adenomyosis (a condition that produces severe and debilitating chronic pelvic pain, the latter pain of which I have been suffering since 1988—for 30 years). I've been taking Gabapentin for the neuropathy and Naprosyn for the adenomyosis. Both these drugs have potentially nasty side effects, including gastrointestinal problems and adverse cardiovascular effects, including my significantly high blood pressure.
I started taking Protein-Allium daily in hopes that it would provide long-term pain relief equal to or better than the above drugs, but with no adverse side effects. Here are the results to date, using a 10-point pain scale:
For the adenomyosis:
Naprosyn alone pain level 4::10
Naprosyn+ Protein-Allium pain level 2::10
Protein-Allium alone pain level 2-4::10
For the neuropathic pain:
Gabapentin alone pain level 1-2::10
Protein-Allium alone pain level 1-2::10
A few months ago, I ran out of Protein-Allium for a brief period, and then I forgot to take my usual dosage of Naproxen Sodium. The adenomyosis pain came back and was about to climb past 6::10, eight hours after the missed dose of Naproxen Sodium, whereas that did not happen while I was taking the Protein-Allium.
Regarding the neuropathy in my shoulder, when I take Protein-Allium there's no muscle memory ("residual pain"). However, with Gabapentin I always had muscle memory of the pain.
With Protein-Allium, I experience no side effects whatsoever.
(The "muscle memory" described by MY seems to be either a shortcoming of, or a side effect from, the gabapentin treatment.)

6.1.7 Protein-Allium Treatment Reduces HIV Treatment-related Pain

A friend of LW and MY (who I will call "PM") writes:
For 25 years I've had neuropathy in my lower legs, with no feeling whatsoever from my knees down. I took gabapentin, but it had bad side effects (drowsiness). After taking Protein-Allium for just one week, I regained feeling in the bottom of my feet, such that I could tell the difference between standing barefoot on a carpet vs. a tile floor.
I've been HIV-positive for 35 years. About five years ago I developed extremely painful arthritis in all my joints, most likely due to the HIV drugs. On a 10 point pain scale the pain level was 10. I couldn't take NSAIDs because of acid reflux.
Now that I'm taking Protein-Allium daily, the pain level has been reduced from 10 all the way down to 5.5.

6.2 Detoxification Pathways

6.2.1 In Biological Systems, Aldehydes Preferentially Attack Sulfhydryl Groups This is a good place to start the detailed description, because whenever free sulfhydryl (SH) groups are available, they are first in line for being attacked by aldehydes. For example, although 4-HNE will readily react with the amino groups of proteins (i.e. lysines, see FIG. 9A) in the absence of available SH groups, experiments show that for concentrations of HNE from $10^{-5}$ to $10^{-3}$ M, and for a duration of several hours, the 4-HNE will attack "practically only sulfhydryl groups" (i.e. cysteines, see FIG. 8A). Compared to the reaction with amino groups, the reaction with SH groups "takes place much faster, in fact by several orders of magnitude" [Schauenstein, 1977; pages 4-5]. At neutral pH and room temperature, the reaction rate with SH groups is approximately one mole per second.

In FIG. 8A, 8I shows the aldehyde (4-HNE) and 82 shows the protein-aldehyde adduct. The cysteine of a protein is denoted as PrSH where the Pr represents the bulk of the protein and the SH represents the SH group of the cysteine.

Although the α,β-unsaturated aldehydes have two sites that are reactive with cysteine, the Michael addition reaction at the C=C unsaturated site is preferred, with the cysteine eliminating the C=C double bond of the aldehyde (FIG. 8A). This reaction is spontaneously reversible. The other possible reaction would be a Michael addition that has the cysteine eliminating the C=O double bond of the aldehyde. Because the reaction at the C=O site is also spontaneously reversible, the aldehyde is likely to eventually end up at the more favorable C=C site.

In FIG. 9A, 9I shows the aldehyde (4-HNE) and 92 shows the protein-aldehyde adduct. The lysine of a protein is denoted as $PrNH_2$ where the Pr represents the bulk of the protein and the $NH_2$ represents the $NH_2$ group of the lysine.

Because the reaction with an amino group is a Michael addition that is spontaneously reversible (FIG. 9A), any such reactions that occur with protein lysines will soon be reversed, and the aldehyde is likely to next attach to an SH group instead of the previous amino group. Of course, this discussion assumes that the number of available cysteines exceeds the concentration of the aldehyde, otherwise the unmodified cysteines will become depleted, and significant modification to lysines will also be seen.

6.2.2 Low Molecular Weight Thiols Effectively Protect Protein Thiols from Aldehydes Low molecular weight thiols scavenge aldehydes very efficiently, as shown in FIG. 8B, which illustrates the conjugate 85 that forms between allyl mercaptan 84 and 4-HNE 83.

In general, aldehydes are more reactive with the SH groups of small molecular thiols that with any other type of molecule found in biological systems. This is true even in comparison with the SH groups of proteins.

FIG. 10 shows how amazingly effectively small molecular thiols protect the SH groups of proteins within actual Ehrlich ascites tumor cells (from FIG. 3.10 of [Schauenstein, 1977]). The aldehyde being used, 4-hydroxypentenal (HPE), is similar in structure and reactivity to 4-HNE. The plotted lines show the percentage decreases of:

Low molecular weight thiols (primarily glutathione) 41
Protein sulfhydryls 42
Inhibition of glycolysis (e.g. enzyme activity) 43
Inhibition of respiration (e.g. $O_2$ consumption) 44

For intracellular concentrations of HPE up to a molar ratio of 0.6 (mol/mol of thiols), the low molecular weight thiols gradually become depleted, but there is no visible effect on protein sulfhydryls or enzyme activities. Only after the low molecular weight thiols are more than 80% depleted do the protein sulfhydryls even start to become affected. And only after 100% of the low molecular weight thiols are depleted and 30% of the protein sulfhydryls have been depleted (by adduct formation) does enzyme activity become affected.

The authors' primary explanation for this is that:

"The preferred reaction of the NPSH [the low molecular weight thiols] may be explained by their greater accessibility to HPE [the aldehyde], whereas the $PSH_s$ [the soluble protein thiols] are partly more difficult of access or not accessible at all (masked sulfhydryl groups), that is to say they remain less reactive, because of the structure of the proteins and the cell compartments."

But I think that another reason is that the level of protein adducts remains so low is that there is a continuous transfer of aldehydes from whatever protein adducts that do form to the low molecular weight thiols that are floating around within the cytosol of the cell. This is the "transglycation" process that has been shown to transfer the glucose (aldehyde) group from protein-glucose conjugates to free glutathione molecules, thereby repairing the glycated proteins [U.S. Pat. No. 7,678,833].

Note that when the low molecular weight thiols are not depleted, the protein SH groups are essentially fully protected from modification by the aldehyde. But when the small molecular weight thiols become fully depleted, the protein SH groups are essentially completely unprotected.

Note that in addition to protecting the protein cysteines, the low molecular weight thiols will protect the protein lysines.

6.2.3 Other Types of Antioxidants do not Protect Proteins from Aldehydes, and in Fact can Make Things Worse Although "SH" based antioxidants such as cysteine and glutathione are protective, other commonly used antioxidants such as Vitamin A, Vitamin C, and Vitamin E provide no protection, and can actually make things worse.

Although vitamin C and glutathione in many ways work together and vitamin C can partially substitute for glutathione as an antioxidant, excessive vitamin C consumption has been shown to significantly decrease the glutathione content of cells. This effect has been utilized in a clinical trial where the goal was to increase the cytotoxicity of the chemotherapeutic drug arsenic trioxide (which is normally detoxified by glutathione within cells) against the cancer multiple myeloma [Bahlis, 2002]. A daily dosage of 1000 mg of vitamin C caused significant glutathione depletion, resulting in a mean percentage decrease of 60% among the patients.

6.2.4 Reactions Between Aldehydes and Thiols Also Occur in Hydrophobic Environments The aldehydes that are formed as lipid peroxide degradation products are sufficiently water soluble to enter the cytosol of the cell and diffuse to diverse targets (including nuclear DNA). This has led most researchers to conduct their in vitro experiments in aqueous systems instead of non-polar oils or solvents. They have firmly established that aldehydes rapidly react with thiols in water, but leave the question of whether such reactions also can occur in non-polar, aprotic environments such as within lipid-based membranes.

However, there is experimental evidence that aldehydes can participate in Michael addition reactions with both cysteine and lysine residues of proteins in hydrophobic environments within cells and also in a model system using an nonpolar aprotic solvent (hexane). The enzyme fructose-1,6-bisphosphatse is inactivated by the aldehyde o-phthaladehyde which creates an irreversible intra-protein cross-link between a cysteine residue and a nearby lysine residue. Because the "molar transition energy" can be used to determine the degree of polarity in the microenvironment of the cysteine and lysine residues participating in the reaction, the measured molar transition energy of the adduct (121 kJ/mol) was well matched to that which was obtained from an analogous model reaction performed in hexane (121 kJ/mol), indicating that the environment within the protein where the reaction occurs must be a hydrophobic environment [Puri, 1988]. Clearly, in the hydrophobic environment the sulfhydryl group of the cysteine is not ionized (i.e. it is an SH instead of an S⁻) and the amino group of the lysine is not ionized (i.e. it is an $NH^2$ instead of an $NH^{3+}$). Therefore, it has been demonstrated that aldehydes are capable of reacting with the non-ionized cysteines and lysines of proteins that are located within lipid environments such as cellular membranes.

6.2.5 Aldehyde Adduct Formation With Protein Lysine Residues

In the absence of low molecular weight thiols, adducts can readily form between aldehydes and protein lysine residues ($PrNH_2$) by a Michael addition reaction, as shown in FIG. 9A.

The aldehyde 4-HNE (91 of FIG. 9A) will react with the lysine amino group ($NH_2$) of a protein (Pr) with the nitrogen of the amino group bonding to one carbon atom of the aldehyde's C═C double bond and one of the two H atoms of the amino group bonding with the other carbon atom of the (now former) double bond. As shown in 92 of FIG. 9A, the adduct is attached to the Nitrogen atom of the protein by a single bond, and the nitrogen atom still retains one of the hydrogen atoms.

6.2.6 Most Protein-Aldehyde Adducts are Protein Carbonyls

As shown in 92 of FIG. 9A, (and also in 82 of FIG. 8A) the protein-aldehyde adduct includes an exposed oxygen that is double bonded to a carbon (a carbonyl group, PrC═O). The most widely used marker for oxidative damage to proteins is the introduction of carbonyl groups.

6.2.7 Protein Repair by Low Molecular Weight Thiols (e.g. Mercaptans)

Mercaptans are low molecular weight thiols that are well suited for repairing aldehyde-modified proteins via transglycation. FIG. 8B shows that allyl mercaptan 84 can exchange with the protein in the 4-HNE-protein adduct 83 to form the 4-HNE-allyl mercaptan conjugate 85 instead (with the protein emerging fully repaired as PrSH).

Similarly, FIG. 9B shows that allyl mercaptan 94 can exchange with the protein in the 4-HNE-protein adduct 93 to form a 4-HNE-allyl mercaptan adduct 95 instead (with the protein emerging fully repaired as $PrNH_2$). Because the aldehyde has much greater affinity for the SH group of the mercaptan than it does for the $NH_2$ group of the protein, the reaction is rapid and is almost irreversible in practice.

The reaction that is being called "transglycation" here is similar to the well-known nucleophilic substitution reaction (where the more "electron rich" nucleophile attacks a molecule that contains a less electron rich nucleophile (which when it leaves is called the "leaving group"). In this case the attack comes from the SH group of the mercaptan which attaches to the aldehyde, and the leaving group is the entire protein.

6.3 TRPA1 as a Target for Preventing and Treating Pain

6.3.1 The Activation and Recovery of TRPA1 is Cyclical

In normal operation, after a TRPA1 channel becomes fully activated it enters a refractory period during which it cannot become activated again. After the refractory period, this TRPA1 channel is presumably in a state that is similar to its initial state before the earlier activation. In other words, one function of the refractory period is to "reset" TRPA1.

The formation of disulfide bonds involving at least some cysteines within TPRA1 is implicated by the nature of agonists such as diallyl disulfide (whose only possible means of activating TRPA1 is by forming a mixed disulfide with cysteine), by an experimentally verified mechanism for regulating channel conductance [Andersson, 2008] and by the experimental detection of disulfide bonds within the TRPA1 protein itself [Wang, 2012].

Resetting the TRPA1 disulfides back to cysteines requires a reductant such as glutathione. During its closed state, the pore diameter is much to small (e.g. 2 angstroms, FIG. 6) for a molecule like glutathione to pass through the pore to get to the critical cysteines, but when the channel is fully open, it becomes highly conductive (FIG. 5A (which is derived from FIG. 7C of [Banke, 2010]) and less selective (FIG. 5B). In other words, these critical cysteines are surrounded by the hydrophobic interior of the TRPA1 protein and are not accessible for reduction (or for transglycation) by hydrophilic thiols such as glutathione, except for when the pore is fully open.

Figure 1:
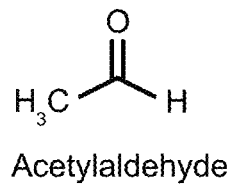
FIG. 1 shows the molecular structure of acetylaldehyde.
Figure 2:
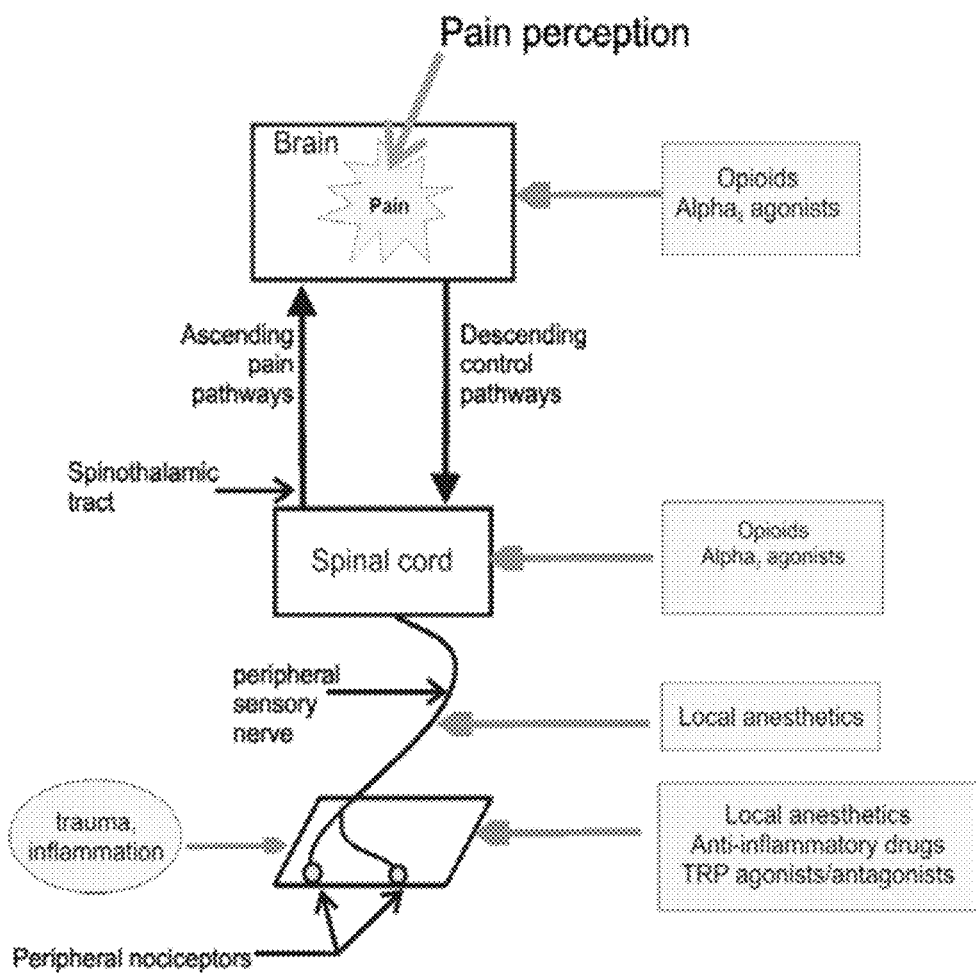
FIG. 2 shows the pain pathway (from FIG. 2 of [Salat, 2013]).

It has been experimentally shown that the TRPA1 channel can pass molecules that are larger than glutathione when its pore is fully open [Chen, 2009]. The molecule "Yo-Pro" is a fluorescent dication (with 2 charged $N^+$ sites) that is used to test for the presence of large diameter pores in cellular membranes because it is too positively charged to otherwise pass through the membranes. The inactivated TRPA1 channel does not pass Yo-Pro into the neuron, but when fully activated, Yo-Pro enters the neuron at a significant rate (FIG. 1B of [Chen, 2009]). Yo-Pro measures 376 Daltons but glutathione measures only 307 Daltons. Given that Yo-Pro can enter (and pass through) the open pore, the smaller glutathione molecule should be able to enter (and react with) the cysteines that line the pore.

6.3.2 Lipophilic Mercaptans for Preventing and Treating Pain

Lipophilic mercaptans are not commonly present in biological systems. The most common low molecular weight thiols are the amino acids cysteine and homocysteine. If they weren't amino acids, they might have been named mercaptans. In fact, one name for cysteine is (R)-2-Amino-3-mercaptopropanoic acid and one name for homocysteine is (S)-2-Amino-4-mercaptobutyric acid. Both of these are highly hydrophilic. The computed Log P for cysteine is −2.5 (it partitions into water vs. oil by ~300 to 1). Homocysteine is almost 10× more hydrophilic than cysteine (computed Log P=−3.4).

The tri-peptide glutathione is also a low molecular weight thiol that has a high concentration in biological systems, but it is too large to be considered a mercaptan and it is even more hydrophilic (computed Log P=−4.5).

The original paper that reported 3 cysteines (and a lysine) are critical for the chemical activation of TRPA1 [Hinman, 2006, see section 3.2.4] referred to "specific cysteine side chains located within the putative cytoplasmic N-terminal domain of the channel" which is diagrammed in FIG. 7 (from FIG. 3a in Hinman). The cylinders represent the six transmembrane helices. The cysteines are represented as dots along the amino acid chain of the protein. The darker dots (colored blue in the original) are for the non-essential cysteines while the lighter dots (colored red in the original) are for the 3 three cysteines that are essential for TRPA1 functionality. The two dashed lines in the figure bracket 6 putative cytoplasmic cysteines (3 of which are essential).

They also state that chemical activation "correlates agonist properties with membrane permeability and cysteine reactivity, consistent with the notion that TRPA1 gating by agonists is mediated by the identified cytosolic cysteines". The model that the chemical agonist crosses the membrane and then finds the cysteines from the cytosolic side continues to permeate the literature on TRPA1.

Thanks to the paper that determined the physical structure of TRPA1 to ~4 angstrom resolution ([Paulsen 2015], see section 3.2.5 above) we now know that the critical cysteines are almost dead-center in the middle of the protein, near the intersection of the transmembrane helices and the "ankyrin repeats" (total of 4) that dominate the cytoplasmic portion of the channel. Thus they are near the bottom of the "lower gate" that is shown in FIG. 6. Although the channel is considered to be aqueous, in the closed state it is only a few angstroms in diameter, and is surrounded by the hydrophobic interior of the protein. Even so, they state that "TRPA1 agonists are potent electrophiles that activate the channel through covalent modification of conserved cysteine or lysine residues within the cytoplasmic N terminus" (emphasis added).

The following list of agonists (those illustrated in FIG. 3 and FIG. 4) shows that the majority significantly lipophilic:

| Compound | Computed LogP |
| --- | --- |
| Acrolein | 0 |
| Allicin | 1.3 |
| Allyl Isothiocyannate (AITC) | 2.4 |
| Cinnamaldehyde | 1.9 |
| Diallyl disulfide | 2.2 |
| Formaldehyde | 1.2 |
| 4-hydroxy-2-nonenal (4-HNE) | 1.7 |
| Ligustilide | 2.7 |
| Perilla ketone | 2.8 |
| Piperanine | 3.1 |
| Umbellulone | 1.6 |
| Velleral | 3.0 |
| 15d-PGJ$_2$ | 5.0 |
| Average | 2.2 |

The α,β-unsaturated aldehydes contain one (or more) carbonyls and one (or more) carbon-to-carbon double bonds which are especially reactive with the protein amino acids cysteine and lysine. Among the aldehydes that are produced in vivo, acrolein is the most reactive (pure acrolein is self-explosive!) but 4-HNE (4-hydroxy-2-nonenal) seems to be the most researched and therefore is chosen to be our model aldehyde.

Other than acrolein, these all partition at least 10 to 1 into the lipid environment instead of the aqueous environment. And even the acrolein is completely lipid soluble. Because acrolein is the most reactive α,β-unsaturated aldehyde, it may not need the "membrane concentration effect" of having a large Log P in order to be a significant activator of TRPA1.

The most lipophilic compound, 15d-PGJ$_2$ (a prostaglandin), is ~10 more active than 4-HNE, perhaps because of the "membrane concentration effect" of its high Log P.

6.3.3 Lipophilic Mercaptans Also Detoxify Hydrogen Peroxide

Because of the role that hydrogen peroxide has been shown to play in the rapid development of secondary hyperalgesia (see Section 3.2.7 above), its detoxification by lipophilic mercaptans can contribute significantly to their short term analgesic effects. In this section, hydrogen peroxide is denoted as HOOH (instead of the usual H$_2$O$_2$) and water is denoted as HOH because this better illustrates the detoxification reaction.

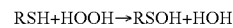

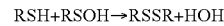

Thus the peroxide becomes reduced to two water molecules and the two mercaptans becomes oxidized to a disulfide. Because oxygen and sulfur are in the same column of the periodic table, they have similar reaction properties (but different rate constants), including the ability to participate in exchange reactions. Although the first step is slower than a thiol disulfide exchange reaction, the resulting sulfenic acid (RSOH) is very reactive and the second exchange reaction is nearly instantaneous. Also, both steps are effectively irreversible, resulting in a relatively efficient (for a nonenzymatic) detoxification process.

If the lipophilic mercaptan has a high Log P, its disulfide is likely to have an even higher Log P. The disulfide from allyl mercaptan has a Log P of 2.2 (a concentration in lipids of about 160 times its concentration in water). The disulfide from propyl mercaptan has a Log P of 2.7 (a concentration in lipids of about 500 times its concentration in water).

These values may seem high, but the disulfides actually leave the membrane at a sufficient rate for them be readily reduced back to mercaptans via exchange reactions with intracellular glutathione. In round numbers, the volume of the cellular membrane is only 1/1000 of the total volume of the cell. Therefore, for propyl mercaptan (partitioning 500 to 1), the total amount inside the cell is actually ~2× the total amount in the membrane. If the disulfide wasn't subject to reduction, each molecule would slowly diffuse between both solvents, spending ~⅓ of the time in the membrane. In practice, the disulfide molecule will tend to become rapidly reduced in the cytosol, and there will be a net flow of mercaptans into the membrane and of disulfides into the cytosol.

6.3.4 Lipophilic Drugs that Scavenge Aldehydes Reduce Pain

The drugs Hydralazine and Phenelzine are known aldehyde scavengers that have been shown to be effective in reducing formaldehyde induced pain and toxicity [Bai, 2012], [Song, 2010]. The molecular structure of Hydralazine (FIG. 12C) reveals its mechanism of action by showing an NH$_2$ group (like that of a lysine) that the aldehyde can attach to (via a Michael addition reaction. Interestingly, Hydralazine is lipophilic, with a Log P of 0.7.

Similarly, Phenelzine (FIG. 12D) has an NH$_2$ group (like that of a lysine) the aldehyde can attach to. Phenelzine is also lipophilic, with a Log P of 1.3.

Figure 12A:
Figure 12B:
Figure 12C:
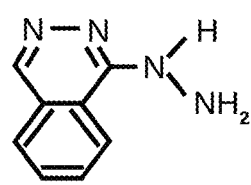
Figure 12D:
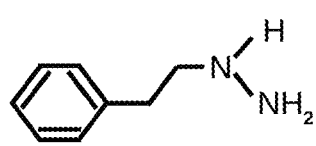
Figure 12E:
Figure 12F:

Interestingly, Gabapentin also has an NH$_2$ group (like that of a lysine) that the aldehyde can attach to. And it is lipophilic, with a measured Log P of 1.2. Gabapentin was designed to be a lipophilic GABA neurotransmitter analog (so it can diffuse through the blood-brain barrier) but also be soluble in water (so it has good bioavailability) [Goa, 1993]. As shown in FIG. 12E, when Gabapentin is in an aqueous environment, the amino group and the carboxyl group are both ionized and located next to each other resulting in good solubility in water, but when transitioning into a lipid environment, the H+ of the ionized amino group can transfer to the adjacent carboxyl group, producing a non-ionized molecule with good solubility in lipids.

The precise mechanisms by which Gabapentin produces its analgesic actions are reported to be unknown by its manufacturer Pfizer. But it is clear to me from its molecular structure that it will function as an aldehyde scavenger, and that this will give it analgesic properties. (Compare FIG. 12E with FIG. 12C and FIG. 12D to see the "$NH_2$ coupled with a lipophilic ring" commonality between Gabapentin and Hydralazine and Phenlzine.)

Compared to the reaction with amino groups, the reaction with SH groups "takes place much faster, in fact by several orders of magnitude" [Schauenstein, 1977; pages 4-5]. Therefore, low molecular weight lipophilic mercaptans will be much more effective at scavenging aldehydes (and thereby reducing pain) than Hydralazine, Phenelzine and Gabapentin are.

6.3.5 Measurements of Pain Sensitization

Pain sensitization is best measured by stimulus perception thresholds because these can be reliably compared between different individuals whereas perceptions of pain intensity are inherently subjective. For mechanical sensitization, measurement of the tactile threshold (whether mechanical pressure is felt at all) is one alternative because the tactile threshold depends on sensitization [Riquelme, 2016]. One advantage of this technique is that there is no need to administer any pain to the subject.

The use of "von Frey hair" fibers in a clinical setting is common for the measurement of sensation threshold variations associated with conditions such as diabetic neuropathy and therefore is a preferred method for this test. For example, the Touch Test Sensory Evaluator Kit from Stoelting Co., Wood Dale, Ill. is a set of 20 probes that has a long history of effective use in clinical settings.

Tactile thresholds for healthy subjects, measured using the gentler (smaller diameter) von Fray hairs from the set, are known and can be used for comparison [Moharic, 2014].

Alternatively, the subject's pressure pain threshold can be measured, either by using the stiffer (larger diameter) von Frey hairs from the set or by using a digital dynamometer [Riquelme, 2016].

Pain sensitization also affects thermal pain thresholds, particularly for "cold pain". The human cold pain threshold is set by TRPA1 and is normally ~5 degrees C., but becomes ~17 degrees C. when sensitized [Obata, 2005]. Therefore, a temperature of (for example) 10 degrees C. would be perceived as cold (but not painful) without sensitization but it will be perceived as painful if the subject's TRPA1-expressing neurons are sensitized.

Note that if the subject presents with localized pain, (e.g. in the left shoulder), the pain sensitivity should also be measured on the contralateral side (e.g. on the right shoulder), to serve as a reference for determining whether there is localized pain sensitization (e.g. for one dermatome but not its contralateral one).

6.4 Pharmacological Intervention Options

6.4.1 Mercaptans Themselves are Poorly Suited for Direct Administration

Mercaptans by themselves are extremely smelly [O'Mullan, 2007] and taste horrible. But the smell and taste can be minimized by forming a mixed disulfide between the mercaptan and a larger molecule. The mixed disulfide gets rid of the exposed SH group and it also reduces the volatility of the compound. For example, allyl mercaptan is an oily liquid that is easily smelled when it is exposed to air, but if it is disulfide bonded to a solid composition the volatility can be effectively eliminated.

In U.S. Pat. No. 7,678,833 compositions are disclosed that utilize a dietary protein (e.g. whey protein) with a mercaptan (e.g. allyl mercaptan) disulfide bonded to the cysteine residues of the protein as a way of administering allyl mercaptan with significantly less taste and smell. The allyl mercaptan is only released from the protein when the protein is digested. But because the amount of cysteine is only ~2% of the protein by weight, the amount of allyl mercaptan that can be contained in the capsule is limited by the bulk of the protein. A capsule containing 500 mg of whey protein can support up to 10 mg of allyl mercaptan from garlic oil. Capsules of this sort were made experimentally starting in 2003 and entered commercial production in 2009.

A higher dosage capsule was developed that uses the mixed disulfide formed from N-acetylcysteine and propyl mercaptan (derived from onion oil). When mixed in water, the N-acetylcysteine dissolves, but the onion oil remains on the surface (at first). As mixing proceeds, the mixed disulfide forms and it is water soluble. The mixing (and mixed disulfide formation) completes when the onion oil has fully disappeared. Drying the mixture produces a white solid that is easily ground into a powder. For the dietary supplement, rice protein powder is included in the mixture to further bind the mixed disulfides and reduce the taste and smell. Drying this mixture produces an off-white solid that is easily ground to form a powder. A capsule containing 250 mg of rice protein with 48 mg of onion oil and 88 mg of N-acetylcysteine (plus enough magnesium to balance the pH) entered commercial production in 2014. These are the "Protein-Allium" capsules that LW decided to use as an experimental treatment for her ALS, and also were used by the other voluntary evaluators that are quoted herein.

More recently, another protein+ allium supplement has been developed which, in want of another name, I will call "AlliumAll". This supplement is based upon the teachings disclosed in U.S. patent application Ser. No. 15/530,804, which recently received a notice of allowance and is included herein by reference. In summary, allyl mercaptan is combined with a two-to-one molar ratio of N-acetylcysteine to form a molecule that has one N-acetylcysteine bound to the allyl mercaptan by a Michael addition across the former double bond of the allyl mercaptan and the other N-acetylcysteine bound to the allyl mercaptan by a disulfide bond. Because the Michael addition can be located at either end of the former double bond, there are two isomers that are formed (FIGS. 14A and 14B):

S-(3-((2-acetamido-2-carboxyethyl)-disulfanyl)propyl)-N-acetylcysteine

S-(1-((2-acetamido-2-carboxyethyl)-disulfanyl)propan-2-yl)-N-acetylcysteine

The advantage of these molecules is that a dianion is formed in water (e.g. at pH=7) (FIG. 14C) which will readily form a linear-polymer salt with divalent cations (e.g. $Ca^{2+}$ or $Mg^{2+}$) as the mixture dries. This decreases the volatility of these sulfur compounds tremendously. During digestion, this composition readily dissolves and while diluted over time, the Michael addition spontaneously reverses freeing the "extra" N-acetylcysteine from the allyl mercaptan.

The allyl mercaptan can be derived from garlic oil, and a protein that contains cysteine can be added to the mixture (further binding the sulfur compounds within the matrix of the protein when dried) to produce what is my current prototype and probably will become my next-generation protein+allium product.

Note that a final metabolite from the consumption of this composition is allyl mercaptan (a lipophilic mercaptan) even though the composition is not a lipophilic mercaptan itself.

6.5 Further Examples

6.5.1 Example Treatments

A Friend of a Friend, Suffering from Back Pain.
"TM" writes:
Two years ago during a trip to Bhutan, I developed severe back pain that radiated down my leg from my lower back. The pain was so bad that when I got home, I needed a wheelchair at the airport. On a 10 point pain scale, the pain level was 10. It was so bad I couldn't stand up. I visited a chiropractor as well as a physical therapist, but neither provided any relief.
Next stop was an orthopedic surgeon. He prescribed a steel back brace and orthopedic shoes. The back brace at least enabled me to stand up. An MRI showed deterioration in my lower spine. I then received a cortisone injection; it provided minimal benefit.
Finally, I started taking Protein-Allium daily. After about a month, the results were dramatic:
Pain level 1.
I no longer needed to wear the back brace.
Needless to say, I continue taking Protein-Allium to this day. Also, I do as much walking as possible, which relieves some tingling sensations on the soles of my feet.
The experience of TM, along with that of LW, MY and PM (Sections 6.1.5 to 6.1.7 above) indicate that:
Protein-allium supplements are effective at decreasing the intensity of a variety of types of pain including "numbness" pain, neuropathic shoulder pain, adenomyosis (chronic pelvic pain), arthritis, and back pain.
Protein-alluim supplements compare favorably with other treatments for pain, including NSAIDs, an opoid (OxyContin), Gabapentin, and Naprosyn. In general, the supplement has been more effective at treating the pain, has fewer side effects, and has other beneficial effects (e.g. the restoration of foot sensation).

6.5.2 Example Dosages

Methods of treating pain sensitization in a subject in need thereof described herein comprise orally administering an organosulfur composition comprising an effective amount lipophilic mercaptan to a subject in need thereof. An "effective amount of a lipophilic mercaptan" means an amount that leads to measurable and beneficial effects for the subject administered the substance. The effective amount administered according to this disclosure can be determined using standard techniques and may be influenced by the circumstances surrounding the case, including the lipophilic mercaptan administered, the symptom being treated and its status, among other considerations. For example, it is expected that those at risk of developing pain hypersensitivity would consume these compositions on a daily basis, either as a dietary supplement or in nutraceutical foods. Those who already have developed pain hypersensitivity are likely to consume a larger quantity as recommended or prescribed by their doctor to achieve a measurable effect.

In the future, similar compositions could also become available in the form of FDA approved drugs with proven safety and effectiveness for the treatment of specific diseases.

The anticipated viable dosage range is from a minimum of 5 mg to a maximum of 150 mg of the lipophilic mercaptan (within the composition, e.g. the mass of the lipophilic mercapto radicals within the mixed disulfide) per day.

Experience with similar mercaptans has shown a dose-dependent effectiveness range of, for example, a total of 30 mg to 60 mg per day (e.g. for the treatment of chronic arsenicosis, as disclosed in U.S. Pat. No. 7,678,833). For this example, the unit dose (per capsule) was 10 mg, so the daily consumption was 3 to 6 capsules. Because arsenicosis is an extreme case, some other conditions are likely be responsive to daily dosages that are below this.

The upper limit of the range is based on the dosages of mercaptans (or disulfides that metabolize to form mercaptans) that have successfully been used in animal studies. For example, in a study of the prevention of acetaminophen poisoning in mice [Nakagawa, 1989], the dosage of S-allylmercaptocysteine used was up to 500 mg/kg, which would correspond to a dosage of 35000 mg of S-allylmercaptocysteine for a 70 kg adult human (which contains approximately 15000 mg of allyl mercaptan). One percent of this dosage is 150 mg/day.

Note that this upper limit is not based upon the development of negative side effects in humans. Instead it is based on being only 1% of a dosage that has been tested in animals without producing any apparent negative side effects. It is unknown what dosage would produce obvious negative side effects in animals (other than perhaps odor).

The most preferred unit dosage is 25 mg of lipophilic mercaptan per unit dosage (e.g. per capsule, or per serving of a nutraceutical). Less preferred is a unit dosage within the range of 5 to 50 mg. Also less preferred is a unit dosage within the range of 26 mg to 150 mg.

The most preferred daily dosage for healthy adults is 50 mg of lipophilic mercaptan per day (e.g. two unit doses of 25 mg each). Less preferred is a daily dosage within the range of 5 to 49 mg. Also less preferred is a daily dosage within the range of 51 mg to 150 mg.

The most preferred daily dosage for children over the age of 10 is one half of the daily dosage for adults (e.g. one unit dose of 25 mg per day).

6.5.3 Alternative Compositions

The examples above have emphasized the use of lipophilic mercaptans which are present naturally in foods such as garlic, onions, and cabbage or are produced from these during normal food preparation and consumption. In particular, both allyl mercaptan and propyl mercaptan are already approved as food ingredients by the FDA. In addition, garlic oil, diallyl disulfide, onion oil, and dipropyl disulfide (which are all FDA approved for use in foods) metabolize during digestion to form allyl mercaptan or propyl mercaptan. In addition to their natural consumption by populations for millennia, these compounds have commonly been used experimentally without apparent toxicity in animals at at dosages up to 200 mg/kg, which would correspond to a dosage of 14,000 mg for a 70 kg adult human.

For a different lipophilic mercaptan that is being developed for use as a drug, the dosage will likely be determined by animal testing followed by Phase 1 (safety dosage range) and Phase 2 (efficacy and dosage optimization) clinical trials. This is necessary (but not undue) experimentation. Therefore, the actual dosage range for any drug is not known beforehand, but for the claimed family of lipophilic mercaptans it is likely to be somewhere within the range of 1 mg to 1000 mg per day. In other words, it is likely to be in the range of ⅕ as active to 5 times as active than the dietary mercaptans.

Allyl mercaptan has a Log P of 1.2 (e.g. it equilibrates to about 16 to 1 higher concentration in the oil side than in the water of a system with both oil and water). Propyl mercaptan has a Log P) of 1.8 (e.g. it equilibrates to an about 65 to 1 higher concentration in the oil side than in the water of a system with both oil and water). Both of these have been shown to be effective at scavenging aldehydes within membranes.

However, TRPA1 agonists commonly are more lipophilic than this, with the diverse compounds listed above having an average Log P of 2.2. Thus, they are very lipid soluble (Log P>0) and also highly concentrated in lipid membranes and other hydrophobic environments (e.g. >100 times, for Log P>2).

This indicates that a higher Log P could be beneficial for the lipophilic mercaptans intended to scavenge these compounds (and thereby prevent pain). Note that the various aldehydes are commonly produced as breakdown products from lipid peroxidation of cellular membranes, and therefore another place to scavenge these would be at their source (e.g. within the cellular membranes) in addition to within TRPA1 itself.

Therefore, the present invention is not limited to compounds where the lipophilic mercaptan component is either allyl mercaptan or propyl mercaptan. Other lipophilic mercaptans are likely to also be safe and beneficial.

Because the lipophilic mercaptans can be expected to occasionally form mixed disulfides with glutathione, it is desirable to limit their molecular mass to 200 g/mol or less. This is because if the molecular mass was greater than this, there could be the possibility that these "glutathione conjugates" would be excreted from the cell by a "multidrug resistance protein" (MRP).

Multidrug resistance proteins are also known as the "GS-X pump" because it will pump any compound "X" out of the cell provided that the "X" becomes conjugated with glutathione and provided that "X" exceeds a molecular mass of approximately 200. The
GS-X pump has been extensively studied due to its role in the detoxification of various anti-tumor chemotherapeutic drugs, such as Cisplatin (whose molecular mass is 301 g/mol), thereby reducing their effectiveness (QP606.G59G59:199). Tumor cells with increased expression of the GS-X pump are termed "multidrug resistant".

Another consideration is that many molecular receptors respond selectively to various organic ring structures. In order to avoid the unintentional recognition of the lipophilic mercaptan by some type of receptor (e.g. an untended side effect), it is desirable to not include any ring structures in the structure of the lipophilic mercaptan.

In general, any lipophilic mercaptans of the invention should be an organic molecule (i.e. include a backbone of carbon and also include hydrogen atoms along with the other atoms in the molecule), the carbon backbone can be branched, but it cannot have any rings. In other words, the molecule must have a single SH group, optionally have other groups attached to the carbon backbone (branching is not excluded), and have a molecular mass of 200 g/mol or less.

These examples are illustrative and the invention is not intended to be limited to these examples.

What is claimed is:

1. A method of treating pain sensitization in a subject with allodynia, said method comprising orally administering to the subject with allodynia an organosulfur composition comprising an effective amount of a mixed disulfide of allyl mercaptan disulfide bonded to rice protein or whey protein;
   wherein said allyl mercaptan reacts with an aldehyde within the lipid membranes of said subject, said aldehyde being in the form of an aldehyde or in the form of a protein-aldehyde adduct, to produce a molecular conjugate of said allyl mercaptan and said aldehyde;
   thereby decreasing the pain sensitization effect of said aldehyde.

2. The method of claim 1 where said administration of said oragnosulfur composition produces a decrease in the amount of protein carbonyls within TRPA1 non-specific cation channel proteins of nociceptive neurons.

3. The method of claim 1 where said administration of said organosulfur composition produces a decrease in the amount of hydrogen peroxide within nociceptive neurons.

4. The method of claim 1 where said organosulfur composition is a dietary supplement.

5. The method of claim 4 where said allyl mercaptan is derived from garlic oil.

6. The method of claim 4 where said dietary supplement is in the form of a capsule or tablet.

7. The method of claim 4 where said dietary supplement is in the form of a beverage.

8. The method of claim 4 where the unit dosage of the disulfide bonded allyl mercaptan within said organosulfur composition is within the range of 5 mg to 150 mg.

9. The method of claim 8 where the unit dosage of the disulfide bonded allyl mercaptan within said organosulfur composition is within the range of 5 mg to 50 mg.

10. The method of claim 8 where the unit dosage of the disulfide bonded allyl mercaptan within said organosulfur composition is within the range of 25 mg to 150 mg.

11. The method of claim 1 where said organosulfur composition is a nutraceutical.

12. The method of claim 11 where the unit dosage of the disulfide bonded allyl mercaptan within said organosulfur composition is within the range of 5 mg to 150 mg.

13. The method of claim 1 where said organosulfur composition is a drug.

14. The method of claim 13 where said organosulfur composition is administered in an amount within the range of 1 mg to 1000 mg per day.

15. The method of claim 1 where said subject in need thereof has been diagnosed with the ALDH2-2 allele of the gene encoding the aldehyde dehydrogenase 2 (ALDH2) protein.

* * * * *